(12) United States Patent
Kim et al.

(10) Patent No.: US 10,871,474 B2
(45) Date of Patent: Dec. 22, 2020

(54) SYSTEM AND METHOD FOR ANALYZING BIOLOGICAL FLUID IN MULTIPLE CUVETTES

(71) Applicant: BODITECH MED INC., Chuncheon-si (KR)

(72) Inventors: Byeong Chul Kim, Chuncheon-si (KR); Bong Suk Moon, Chuncheon-si (KR); Younghaeng Lee, Chuncheon-si (KR); Ju Hyoung Bang, Chuncheon-si (KR); Nam Chul Ha, Seoul (KR); Jae Un An, Incheon (KR)

(73) Assignee: BODITECH MED INC., Chuncheon-si (KR)

( * ) Notice: Subject to any disclaimer, the term of this patent is extended or adjusted under 35 U.S.C. 154(b) by 560 days.

(21) Appl. No.: 15/817,089

(22) Filed: Nov. 17, 2017

(65) Prior Publication Data
US 2018/0074027 A1    Mar. 15, 2018

Related U.S. Application Data

(63) Continuation-in-part of application No. 15/574,131, filed as application No. PCT/KR2016/005050 on May 13, 2016, now Pat. No. 10,670,499.

(30) Foreign Application Priority Data

May 14, 2015 (KR) .................... 10-2015-0067278
May 12, 2016 (KR) .................... 10-2016-0058165

(51) Int. Cl.
*G01N 35/00* (2006.01)
*G01N 30/95* (2006.01)
(Continued)

(52) U.S. Cl.
CPC .............. *G01N 30/95* (2013.01); *B01L 3/502* (2013.01); *G01N 21/03* (2013.01); *G01N 30/91* (2013.01);
(Continued)

(58) Field of Classification Search
CPC ............ G01N 35/109; G01N 35/1095; G01N 21/8483; G01N 2021/0325;
(Continued)

(56) References Cited

U.S. PATENT DOCUMENTS

2012/0122231 A1  5/2012  Tajima
2014/0023568 A1  1/2014  Hong et al.
(Continued)

FOREIGN PATENT DOCUMENTS

KR  10-2003-0065341 A  8/2003
KR  10-2010-0007720 A  1/2010
(Continued)

OTHER PUBLICATIONS

International Search Report dated Aug. 30, 2016 of PCT/KR2016/005050 which is the parent application and its English translation—4 pages.
(Continued)

*Primary Examiner* — Christopher L Chin
(74) *Attorney, Agent, or Firm* — Knobbe Martens Olson & Bear LLP

(57) ABSTRACT

Disclosed is a station, for testing an analyte in a sample, enabling accurate and quick reaction and analysis of the sample and a reagent in one apparatus. To this end, the present disclosure provides a station, which is for testing a sample by means of inserting a cuvette, having a standby chamber on which a collecting member is placed, a sample chamber, a reagent chamber and a detection unit. The station comprises: a housing which has an input/output part into
(Continued)

which a cuvette is inserted; a driving unit which is provided inside the housing, horizontally moves the cuvette, vertically moves a collecting member, reacts a sample in a sample chamber and a reagent in a reagent chamber, and injects a reaction result thereof into a detection unit; and an optical reader which is provided on the horizontal movement path of the cuvette and is for analyzing the reaction result.

14 Claims, 37 Drawing Sheets

(51) Int. Cl.
*G01N 35/10* (2006.01)
*G01N 21/03* (2006.01)
*G01N 30/91* (2006.01)
*G01N 35/02* (2006.01)
*B01L 3/00* (2006.01)
*G01N 33/53* (2006.01)
*G01N 35/04* (2006.01)
*G01N 21/84* (2006.01)

(52) U.S. Cl.
CPC ....... *G01N 33/5304* (2013.01); *G01N 35/026* (2013.01); *G01N 35/109* (2013.01); *G01N 35/1081* (2013.01); *G01N 35/1095* (2013.01); *B01L 3/5023* (2013.01); *B01L 2200/028* (2013.01); *B01L 2200/16* (2013.01); *B01L 2300/0663* (2013.01); *B01L 2300/0825* (2013.01); *B01L 2400/0406* (2013.01); *G01N 21/8483* (2013.01); *G01N 2021/0325* (2013.01); *G01N 2035/0413* (2013.01); *G01N 2035/0429* (2013.01)

(58) Field of Classification Search
CPC ... G01N 2035/0413; G01N 2035/0429; G01N 2035/00752; G01N 2035/0401; G01N 2035/0436; G01N 2035/0484; G01N 35/00732; G01N 35/026; G01N 35/04; G01N 35/1083; G01N 35/02; G01N 21/13; G01N 21/17; G01N 21/135; G01N 1/14; G01N 1/18; G01N 2001/185; B01L 3/5023; B01L 2200/028; B01L 2200/16; B01L 2300/0663; B01L 2300/0825; B01L 2400/0406; B01L 3/56
USPC ........ 422/63, 65, 66, 67, 64; 436/46, 47, 43, 436/50, 54; 435/286.1, 287.1
See application file for complete search history.

(56) References Cited

U.S. PATENT DOCUMENTS

| | | |
|---|---|---|
| 2014/0170735 A1 | 6/2014 | Holmes |
| 2018/0074027 A1 | 3/2018 | Kim et al. |
| 2018/0128715 A1 | 5/2018 | Kim et al. |

FOREIGN PATENT DOCUMENTS

| | | |
|---|---|---|
| KR | 10-2010-0027389 A | 3/2010 |
| KR | 10-2011-0007699 A | 1/2011 |
| KR | 10-2011-0127386 A | 11/2011 |
| KR | 10-2012-0025580 A | 3/2012 |
| KR | 10-2012-0027359 A | 3/2012 |
| KR | 10-1149357 B1 | 5/2012 |
| KR | 10-2013-0072987 A | 7/2013 |
| KR | 10-2015-0054689 A | 5/2015 |
| KR | 10-2015-0057181 A | 5/2015 |

OTHER PUBLICATIONS

Office Action dated Jul. 17, 2017 in corresponding Korean Patent Application No. 10-2016-0058165—8 pages.

FIG. 7D
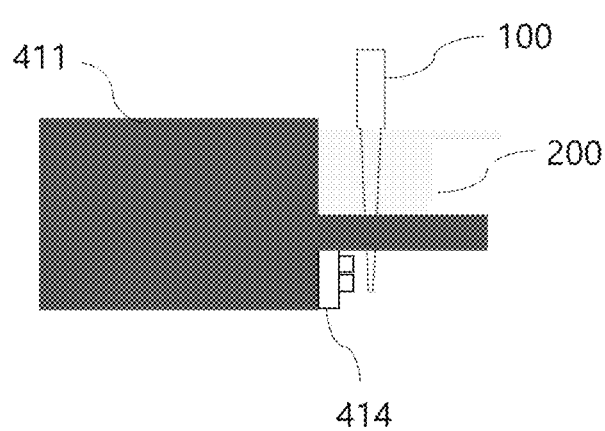
Side View
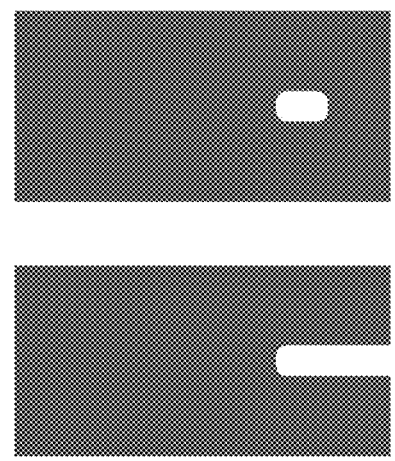
TOP view

FIG. 16
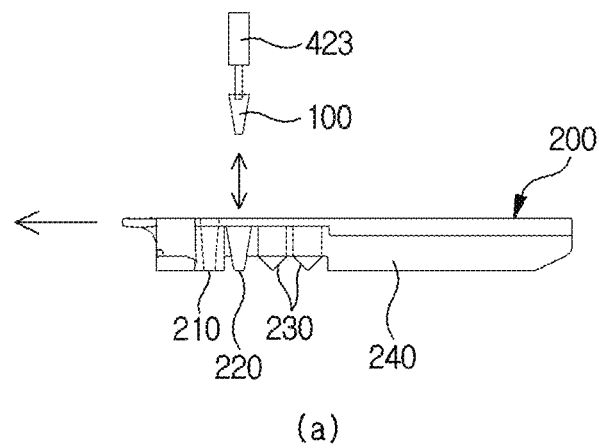
(a)
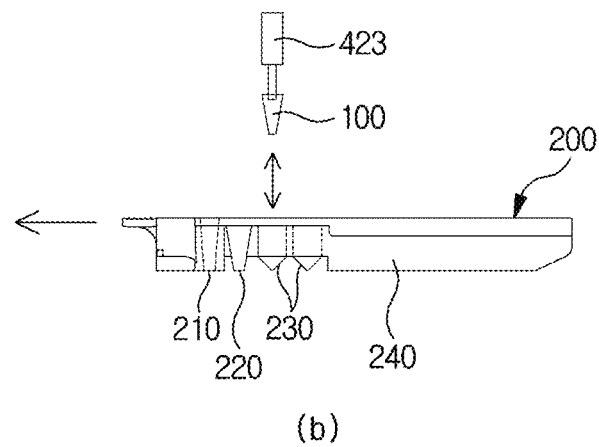
(b)
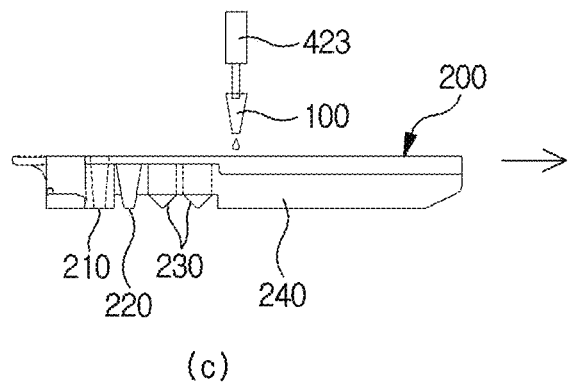
(c)

SYSTEM AND METHOD FOR ANALYZING BIOLOGICAL FLUID IN MULTIPLE CUVETTES

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present disclosure relates to a system for detecting a specific component in a biological sample or the like.

Discussion of the Related Technology

Generally, with the development of medical technology and various related technologies, testing particular target substances such as blood cells, nucleic acids, proteins and antigens comprised in specific biological samples such as blood has been widely used for such as diagnosis of diseases. In the test, after collecting samples for analysis, the presence or absence, ratio, amount and the like of various target substances in the collected samples are determined by analyzing and monitoring the target or its changes for which, the collected samples are allowed to react with specific reagents, thereby obtaining information about the presence or absence of a target, the state of disease, and the like.

Korean Patent Application Publication No. 10-2012-0027359 (published on Mar. 21, 2012) discloses the related technology.

SUMMARY

One aspect of the invention provides a method of analyzing biological sample fluid, the method which may include:
placing a plurality of cuvettes in an analyzer, each of the plurality of cuvettes comprising biological sample fluid,
wherein each cuvette comprises an elongated body with multiple wells and a chromatography inlet that are arranged along a longitudinal direction, wherein the multiple wells comprise a sample well into which the sample fluid is loaded for analysis, wherein the multiple wells further comprise at least one reaction well that contains a reaction composition, wherein each cuvette further comprises a chromatographic strip arranged behind the multiple wells in the longitudinal direction, the chromatographic strip comprising one end portion fluid communication with the chromatography inlet such that fluid received through the chromatography inlet is loaded at the end portion of chromatographic strip,
wherein the analyzer comprises:
a cuvette holder configured to receive and hold two or more cuvettes, the cuvette holder being further configured to move along y axis such that cuvettes held in the cuvette holder move all together along y axis when the cuvette holder moves,
a pipette configured to take fluid from a well and release fluid into a well, the pipette being further configured to move along x axis and to move along z axis perpendicular to x and y axes, and
an optical detector for detecting a chemical entity connected to a biomarker in a chromatographic strip, the optical detector configured to move along x axis independently from movement of the pipette;
processing a first sample fluid contained in the sample well of a first one of the plurality of cuvettes placed in the cuvette holder using at least one reaction composition contained in the at least one reaction well of the first cuvette to obtain the first reaction mixture, wherein processing the first sample fluid is performed within a first sample processing time period;
subsequent to processing the first sample fluid, performing chromatography of the first reaction mixture in the first chromatographic strip for a first chromatography time period;
subsequent to performing the chromatography of the first reaction mixture, performing, using the optical detector, optical detection of the first chemical entity connected to a first biomarker in the first chromatographic strip;
subsequent to processing the first sample fluid, processing a second sample fluid contained in the sample well of a second one of the plurality of cuvettes placed in the cuvette holder using at least one reaction composition contained in the at least one reaction well of the second cuvette to obtain the second reaction mixture, wherein the processing the second sample fluid is performed within a second sample processing time period;
subsequent to processing the second sample fluid, performing chromatography of the second reaction mixture in the second chromatographic strip for a second chromatography time period; and
subsequent to performing the chromatography of the second reaction mixture, performing, using the optical detector, optical detection of the second chemical entity connected to a second biomarker in the first chromatographic strip,
wherein, when the first chromatography time period is longer than the second sample processing time period, processing the second fluid sample is performed before the optical detection for the first cuvette while processing the second fluid sample is performed after the optical detection for the first cuvette when the first chromatography time period is shorter than the second sample processing time period.

In the foregoing method,
processing the first sample may comprise:
taking, using the pipette with a first suction tip, the first sample fluid from the sample well of the first cuvette,
releasing, using the pipette with the first suction tip, the first sample fluid into the at least one reaction well of the first cuvette to obtain the first reaction mixture,
taking, using the pipette with the first suction tip, at least a portion of the first reaction mixture from the at least one reaction well,
releasing, using the pipette with the first suction tip, the first reaction mixture into the chromatography inlet of the first cuvette;
wherein processing the second sample comprises:
taking, using the pipette with a second suction tip, the second sample fluid from the sample well of the second cuvette, releasing, using the pipette with the second suction tip, the second sample fluid into the at least one reaction well of the second cuvette, taking, using the pipette with the second suction tip, at least a portion of the second reaction mixture from the at least one reaction well of the second cuvette, and releasing, using the pipette with the second suction tip, the second reaction mixture into the chromatography inlet of the second cuvette;

wherein the first sample processing time period is equal to or longer than a time period from taking the first sample fluid to releasing the first reaction mixture, wherein the second sample processing time period is equal to or longer than a time period from taking the second sample fluid to releasing the second reaction mixture.

Still in the foregoing method, the optical detection for the first cuvette is not performed while processing the second sample fluid. The first sample fluid may be obtained from a first person and the second sample fluid is obtained from a second person different from the first person, wherein the first biomarker is different from the second biomarker. The optical detection of the second chemical entity in the second chromatographic strip may be performed prior to the optical detection of the first chemical entity in the first chromatographic strip. The optical detection of the second chemical entity in the second chromatographic strip may be performed after the optical detection of the first chemical entity in the first chromatographic strip. The method may further comprise moving the cuvette holder along in y axis for placing the first cuvette under the optical detector such that the first chromatographic strip is located at a first optical detection location, wherein while the first chromatographic strip is located at the first optical detection location, the pipette is located at a location immediately above the second cuvette such that the pipette overlaps the second cuvette when viewed along z axis.

Yet in the foregoing method, the method may further comprise, subsequent to processing the second sample fluid, processing a third sample fluid contained in the sample well of a third one of the plurality of cuvettes placed in the cuvette holder using at least one reaction composition contained in the at least one reaction well of the third cuvette to obtain the third reaction mixture, wherein processing the third fluid sample is performed before the optical detection for the first cuvette. The optical detection for the first cuvette and optical detection for the second cuvette are not performed while processing the third sample fluid. The method may further comprise, subsequent to processing the second sample fluid, processing a third sample fluid contained in the sample well of a third one of the plurality of cuvettes placed in the cuvette holder using at least one reaction composition contained in the at least one reaction well of the third cuvette to obtain the third reaction mixture, wherein the optical detection for the first cuvette is performed between performing processing of the second sample fluid and performing processing of the third sample fluid. The optical detection for the second cuvette is not performed while processing the third sample fluid.

Further in the foregoing method, the method may further comprise: before processing the first sample fluid, moving the pipette along z axis to engage the first suction tip; after processing the first sample fluid, moving the pipette along x axis from a pipette location over the first cuvette to a disengagement location of the analyzer; subsequently moving the pipette along z axis to remove the first suction tip from the pipette at the disengagement location; and wherein the pipette moves from the location of the first cuvette to the disengagement location while performing chromatography for the first cuvette and while the cuvette holder is moving along y axis. The method may further comprise: before processing the first sample fluid, moving the pipette along z axis to engage the first suction tip; after processing the first sample fluid, moving the pipette along x axis from a pipette location over the first cuvette to a disengagement location of the analyzer; subsequently moving the pipette along z axis to remove the first suction tip from the pipette at the disengagement location; and subsequently moving the pipette along x axis to another pipette location over the second cuvette different from the first pipette location, wherein the pipette moves from the location of the first cuvette to the location over the second cuvette via the disengagement location while performing chromatography for the first cuvette.

Still further in the foregoing method, the cuvette holder may be referred to as a first cuvette holder, wherein the analyzer may further comprise a second cuvette holder for receiving and holding a plurality of cuvettes, the second cuvette holder being configured to move along y axis independently from the movement of the first cuvette holder such that the plurality of cuvettes in the second cuvette holder moves all together along y axis when the second cuvette holder moves along y axis, wherein process sample fluid is performed in one of the plurality of cuvettes in the second cuvette holder while optical detection is performed in one of the plurality of cuvettes in the first cuvette holder.

The present disclosure provides a system which enables the reaction between a sample and a reagent and the reading/analysis of the reaction product to be performed in a streamlined process in an accurate and rapid manner, and which enables analysis of multiple reactions accommodating plurality of diagnosis kits simultaneously, thereby achieving a multiple diagnoses and analyses and making it possible to simultaneously perform multiple reactions, detection and analysis for several samples, and also which can detect and analyze different fluorescence assays employing a plurality of light sources each having different wavelength enabling multiple assays.

In one aspect, the present disclosure further provides a station for use with a cuvette, to detect an analyte in a sample, the cuvette comprising a sample collection member standby chamber in which a sample collection member is placed, a sample chamber, a reagent chamber, and a detection part, the station comprising: a housing having an input/output part through which a plurality of the cuvettes enter and exit the station, the housing having a space in which the plurality of cuvettes are arranged in parallel in a lateral direction; a first driving unit provided in the housing and configured to move the plurality of cuvettes longitudinally, move the sample collection member in left and right directions so as to position the sample collection member over any one of the plurality of cuvettes, and configured to move the sample collection member vertically so as to allow a sample in the sample chamber to react with a reagent in the reagent chamber, and inject a product of the reaction into the detection part; an optical reader provided on the path of longitudinal movement of the cuvettes and configured to read or analyze detection results from the reaction product; and a second driving unit configured to move the optical reader laterally so as to position the optical reader over any one of the plurality of cuvettes. The present station is optimized for use with a cuvette such as disclosed in FIGS. 21A and 21B.

The first driving unit may comprise: a longitudinal moving unit configured to move the plurality of cuvettes forward and backward so as to position any one of the sample chamber, reagent chamber and detection part of any one of the plurality of cuvettes at a position corresponding to the position of the sample collection member; an vertical moving unit configured to mount to the sample collection member and move the sample collection member upward and downward in and out of any one of the sample chamber, the reagent chamber and the detection part; a laterally moving unit connected to the vertical moving unit and configured to move the sample collection member and the vertical moving unit in left and right directions so as to position the sample collection member over any one of the plurality of cuvettes; and a pump unit configured to apply a suction force or a discharge force when the sample collection member is inserted into any one of the sample chamber, reagent chamber and detection part of any one of the plurality of cuvettes.

The longitudinal moving unit may comprise: a holder which is provided at a position corresponding to the input/output part and in which the plurality of cuvettes are mounted; a longitudinal guiding part configured to guide the holder forward and backward; and a longitudinal driving part configured to apply a longitudinal force to the holder.

The longitudinal guiding part may comprise: a horizontal support configured to support the holder in the housing; a longitudinal guiding rail formed either in a portion of the horizontal support, which contacts with the holder, or in a portion of the holder, which contacts with the horizontal support; and a longitudinal guiding groove formed in either in a portion of the horizontal support, which contacts with the holder, or in a portion of the holder, which contacts with the horizontal support, so as to engage the longitudinal guiding rail.

The longitudinal driving unit may comprise: a first connecting bracket connected to the holder; a ring-shaped first belt to which the first connecting bracket is fixed; a first motor provided on one side of the first belt so as to rotate the first belt; and a first driven pulley provided on the other side of the first belt so as to rotatably support the first belt.

The longitudinal moving unit may be provided in plurality, and the plurality of longitudinal moving units may be driven independently of each other.

The station may further comprise a removal unit disposed between the plurality of longitudinal moving units and configured to separate the sample collection member from the vertical moving unit.

The removal unit may comprise a slider which has a through-hole formed vertically and which is slidably movable in one direction, and the slider may be configured such that when the vertical moving unit moves upward after the sample collection member is inserted into the through-hole, the slider slidably moves so that the sample collection member is separated from the vertical moving unit.

The removal unit may further comprise: a jig having a sliding hole which is formed vertically so as to form a path along which the slide moves slidably, in which the sliding hole extends longitudinally; a waste box disposed below the jig and configured such that the sample collection member separated from the vertical moving unit is dropped into the waste box; and a spring disposed in the sliding hole and configured to apply elasticity between the inner surface of the sliding hole and the slider so as to elastically bias the slider.

The holder may have one or more mounting channels which are arranged in parallel and in which one or more of the cuvettes are inserted and mounted.

The holder may comprise a heater configured to heat the holder, and a temperature sensor configured to sense the temperature of the holder.

The vertical moving unit may comprise a second connecting bracket connected to the laterally moving unit so as to be movable left and right and extending vertically; a vertical guiding rail provided on the second connecting bracket; an arm configured to move upward and downward along the vertical guiding rail; and a vertical driving part connected to the second connecting bracket and configured to apply a force in an upward and downward direction to the arm.

The vertical driving part may comprise: a third connecting bracket connected to the arm and configured to move upward and downward along the vertical guiding rail; a ring-shaped second belt to which the third connecting bracket is fixed and which extends long vertically; a second motor connected to the second connecting bracket and provided on one side of the second belt so as to rotate the second belt; and a second driven pulley connected to the second connecting bracket and provided on the other side of the second belt so as to rotatably support the second belt.

The laterally moving unit may comprise: a laterally guiding part configured to guide the second connecting bracket left and right; and a laterally driving part configured to apply a force in left and right directions to the second connecting bracket.

The laterally guiding part may have: a laterally guiding rail provided to extend long laterally in the housing; and a laterally guiding grove formed in the second connecting bracket and engaging the laterally guiding rail.

The longitudinal driving part may comprise: a ring-shaped third belt to which the second connecting bracket is fixed and which extends long left and right; a third motor provided on one side of the third belt and configured to rotate the third belt; and a third driven pulley provided on the other side of the third belt and configured to rotatably support the third belt.

The pump unit may be configured such that it provides a suction force to the sample collection member when the sample collection member is positioned over any one of the plurality of cuvettes by the laterally moving unit, is positioned over the sample chamber by the longitudinal moving unit, and is inserted into the sample chamber of the cuvette by the vertical moving unit, and the pump unit repeatedly provides a suction force and a discharge force to the sample collection member when the reagent chamber is positioned under the sample collection member by the longitudinal moving unit and then the sample collection member is inserted into the reagent chamber by the vertical moving unit, and the pump unit provides a discharge force to the sample collection member when the detection part is positioned under the sample collection member by the longitudinal moving unit and the sample collection member is inserted into the detection part by the vertical moving unit.

The pump unit may comprise: a tube line formed so as to pass through the arm; and a pump provided in the arm and configured to apply a pumping force to the sample collection member through the tube line.

The second driving unit may comprise: a fourth connecting bracket to which the optical reader is connected; a second laterally guiding part configured to guide the fourth connecting bracket left and right; and a second longitudinal driving part configured to apply a force in left and right directions to the fourth connecting bracket.

The second laterally guiding part may comprise: a second laterally guiding rail provided to extend long laterally in the housing; and a second laterally guiding part provided in the fourth connecting bracket and having a second laterally guiding groove engaging the second laterally guiding rail.

The second longitudinal driving part may comprise: a ring-shaped fourth belt to which the fourth connecting bracket is fixed and which extends long laterally; a fourth motor provided on one side of the fourth belt and configured to rotate the fourth belt; and a fourth driven pulley provided on the other side of the fourth belt and configured to rotatably support the fourth belt.

The station according to the embodiment of the present disclosure as described above may further comprise a display unit provided in the housing and configured to display analysis results obtained by the optical reader.

The station according to the embodiment of the present disclosure as described above may further comprise a chip insertion part which is provided in the housing and into which a chip containing information about a sample filled in the sample chamber is inserted.

The station according to the embodiment of the present disclosure as described above may further comprise an output part provided in the housing and configured to print out the analysis results.

The station according to the embodiment of the present disclosure as described above may further comprise a door provided in the housing and configured to open and close the input/output part.

The station according to the embodiment of the present disclosure as described above may further comprise: a printed circuit board provided in the housing; and a control unit mounted on the printed circuit board and configured to control the first driving unit, the second driving unit and the optical reader.

The optical reader may comprise a plurality of laser light sources and a plurality of filters so as to measure and analyze fluorescent signals having different wavelengths.

The cuvette may further comprise a barcode that encodes the kind of analyte in the sample; the station may further comprise a chip and a chip insertion part into which the chip is inserted; the barcode is interlocked with the chip; and the chip may contain information for driving the station depending on the kind of analyte in the sample.

In another aspect, the present disclosure provides a method of detecting an analyte in a sample by use of the station according to the present disclosure.

The station according to the present disclosure is used with a testing device comprising an integrated reaction and detection means, for example, a cuvette as described below, which is inserted into the station. The station is an integrated system in which a dispensing of a sample, a reaction between a reagent and the sample, a detection of the reaction product, and a reading/analysis of the detection results, are performed in a streamlined fashion in an accurate and rapid manner. Thus, the use of the station according to the present disclosure can increase analysis accuracy and reproducibility of a test while decreasing the time required, and also reduce the steps involved and costs required for the overall analysis. The present station is optimized for use with a cuvette such as disclosed in FIGS. 21A and 21B.

Furthermore, the station according to the present disclosure comprises a holder having a plurality of mounting channels so as to enable a plurality of cuvettes to be mounted in a single holder, and also comprises a plurality of longitudinal moving units configured to accommodate the cuvettes and move the holder, and thus allows multiple diagnoses and analyses to be simultaneously performed in a single system. Accordingly, various tests and diagnoses/analyses may be rapidly performed using the present station to provide accurate diagnoses for a place where tastings and treatments are routinely performed, and thus the time, cost and manpower required for the analysis can be reduced.

In addition, the station according to the present disclosure comprises an optical reader which has light sources having different wavelengths and which can measure fluorescence signals with different wavelengths. Thus, the station according to the present disclosure can be used for assays employing different fluorescence signals. In addition, the optical reader is configured to be movable laterally, and thus each of a plurality of cuvettes can be analyzed independent of each other.

The housing included in the station according to the present disclosure can prevent possible contamination from outside, making it possible to perform more accurate sample analysis. In addition, the station according to the present disclosure comprises driving units that provide vertical and lateral moving forces, and also comprise an optical reader on the path of lateral movement of cuvettes, and thus makes it possible to perform sample analysis in a rapid and simple manner.

In addition, the pump unit included in the station according to the present disclosure can accurately control the amount of sample, reagent or reaction product collected or discharged through the sample collection member.

In addition, the pulley-belt type longitudinal driving unit included in the station according to the present disclosure can prevent vibration and contamination across cuvettes caused by frictions during the lateral movement happened in a gear type, and thus enables more accurate analysis to be performed.

In addition, according to one embodiment of the present disclosure, the holder comprises a heater and a temperature sensor. Thus, a sample in the sample chamber, a reagent in the reagent chamber, and a reaction product in the detection part, can be maintained at suitable temperatures required for analysis.

In addition, according to one embodiment of the present disclosure, the station comprises a display unit so that analysis results can be immediately seen. Thus, rapid analysis can be achieved.

In addition, according to one embodiment of the present disclosure, the station comprises a chip insertion part that makes it possible inputting information in a more rapid and accurate manner compared to inputting sample information through a keyboard.

In addition, according to one embodiment of the present disclosure, the station comprises a print/output part, and thus analysis results can be immediately provided as a document through the print/output part without having to use a separate printer.

In addition, according to one embodiment of the present disclosure, the station comprises a door. Accordingly, the door may be closed during analysis in order to prevent foreign matter from entering the housing, and thus more accurate analysis can be performed.

In addition, according to one embodiment of the present disclosure, the station comprises a control unit, and thus all processes associated with analysis can be automatically performed.

In addition, according to one embodiment of the present disclosure, the cuvette used in the station according to the present disclosure may further comprise a barcode. The barcode contains information about a material (item) to be analyzed and the lot of the cuvette. Accordingly, the station may further comprise a chip interlocked with the barcode. Accordingly, the station can be operated so that optimal analysis can be performed depending on the kinds of various analytes, and thus various analytes can be easily detected by a single station, and the reproducibility and reliability of analysis can also be improved. The barcode retrieves information using a barcode scanner that scans the same.

BRIEF DESCRIPTION OF THE DRAWINGS

FIG. 7D depicts a cross-sectional view schematically showing a state in which a sample collection member is inserted in a cuvette mounted in a holder, and a sensor (attached to the lower side of the holder) for sensing the insertion, and also depicts a top view of the holder.

FIG. 16 shows a process in which the sample chamber, reagent chamber and detection part of a cuvette are positioned over a sample collection member bound to an arm while the cuvette is moved forward by a longitudinal moving unit.

DETAILED DESCRIPTION OF EMBODIMENTS

Figure 1A:
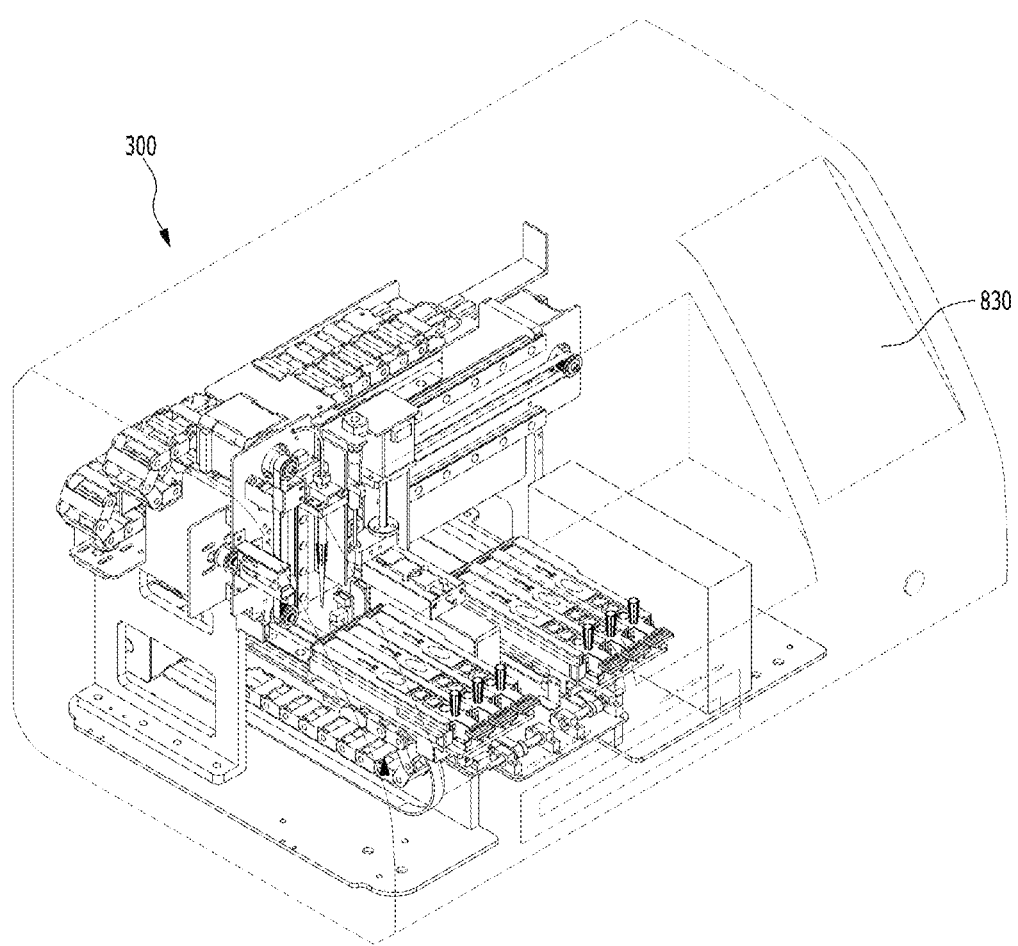
FIG. 1A is a perspective view schematically showing a station according to an embodiment of the present disclosure.

Hereinafter, embodiments of the present disclosure will be described with reference to the accompanying drawings. These embodiments are for illustrative purposes and are not intended to limit the scope of the present disclosure in any way.

Unless specific from the context, the spatially relative terms "under", "backside", "above", "upper", and the like may be used herein for ease of description to describe the relations between one element or component and another element(s) or component(s) as illustrated in the figures. It will be understood that the spatially relative terms are intended to encompass different orientations of the device in use or operation, in addition to the orientation depicted in the figures. For example, in the case where an element shown in the figure is turned over, the element positioned "below" or "under" another element may be placed "above" another element.

The element may also be oriented in the other direction. Thus the spatially relative terms may be interpreted differently depending on the orientations unless specific from the context. For example, "lateral direction" may also be interpreted as "up and down direction", but is not limited thereto.

In the figures, the thickness or size of each element is exaggerated, omitted, or schematically illustrated for convenience in description and clarity. Furthermore, the size and area of each constituent element does not entirely reflect the actual size or area thereof. In addition, the angles and directions mentioned while describing structures of the present disclosure in the embodiments are based on the figures. In the specification, when a reference point and relations of position with respect to an angle in a description on a structure constituting the present disclosure are not clearly mentioned, reference will be made to a related figure.

In the sample testing process, the samples and the reagents used in testing of the samples are protected from external factors and should be used in exact amounts every time the test is performed. This is crucial in obtaining reproducible and accurate results. However, during the testing process, the samples and the reagents may be exposed to an external environment, and for this reason, the samples and reagents be prevented from being contaminated due to the exposures and be used in exact amounts, thereby ensuring the accuracy of testing.

Furthermore, after the reaction between the reagents and the samples, test processes for the detection, reading and analysis of the reaction products be performed sequentially in a single integrated system in an accurate and rapid manner, thereby reducing testing time and costs and reducing the steps and the costs required for overall analysis.

In a typical testing system, only a single diagnostic kit is used per diagnostic test, and thus there is a limit to rapidly performing the testing, analysis and diagnosis of a target analyte.

FIG. 1 is a perspective view schematically showing a station according to an embodiment of the present disclosure.

Figure 4:
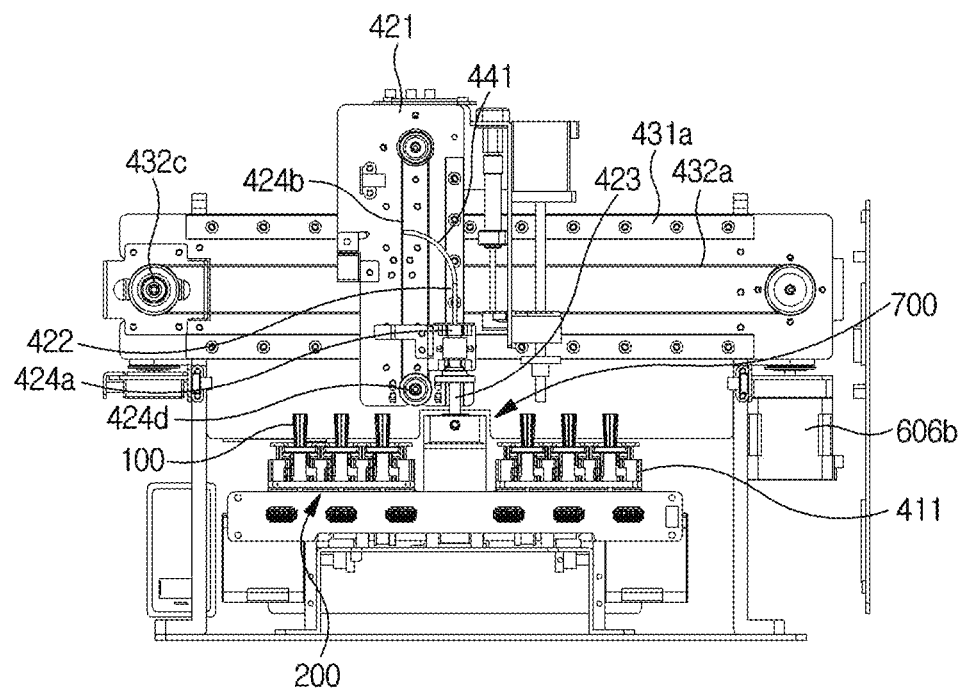
FIG. 4 is a perspective view schematically showing the inside of the station of FIG. 1 in still another direction.
Figure 5A:
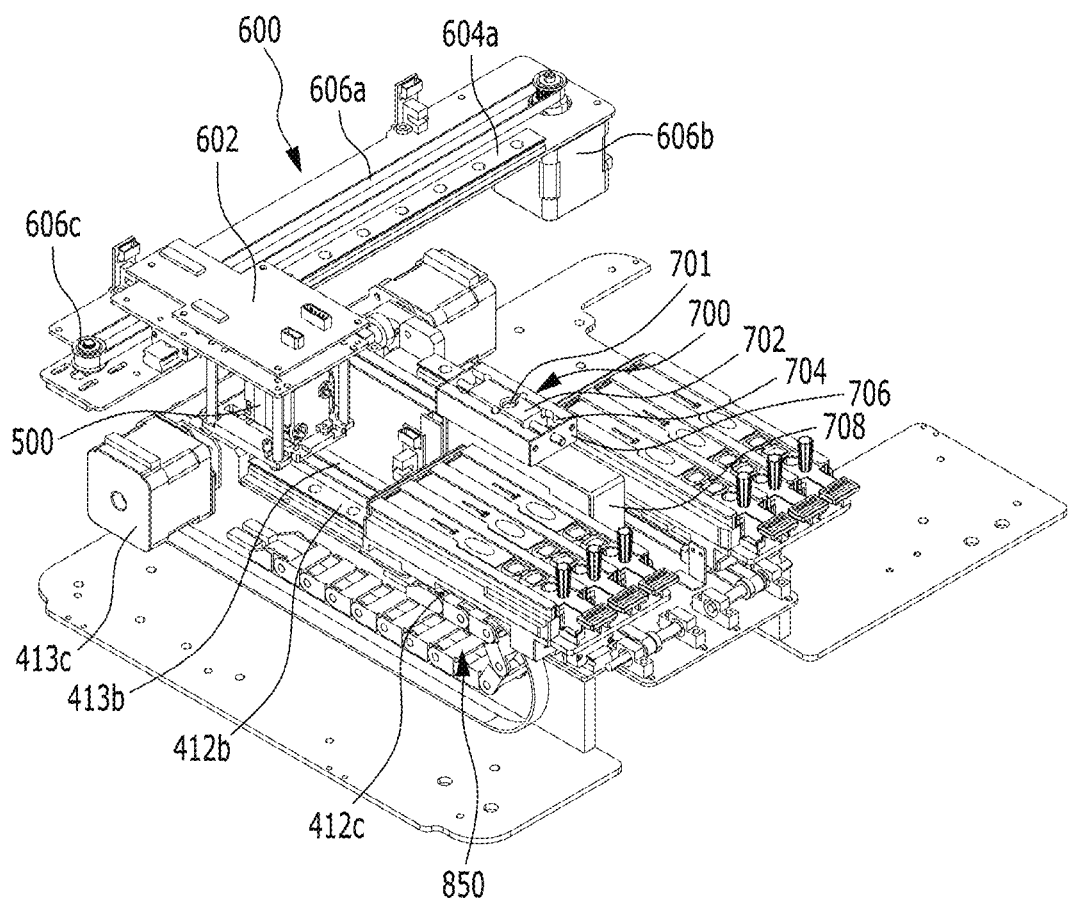
FIG. 5A is a perspective view schematically showing the inside of the station of FIG. 2A while omitting a part thereof.
Figure 5B:
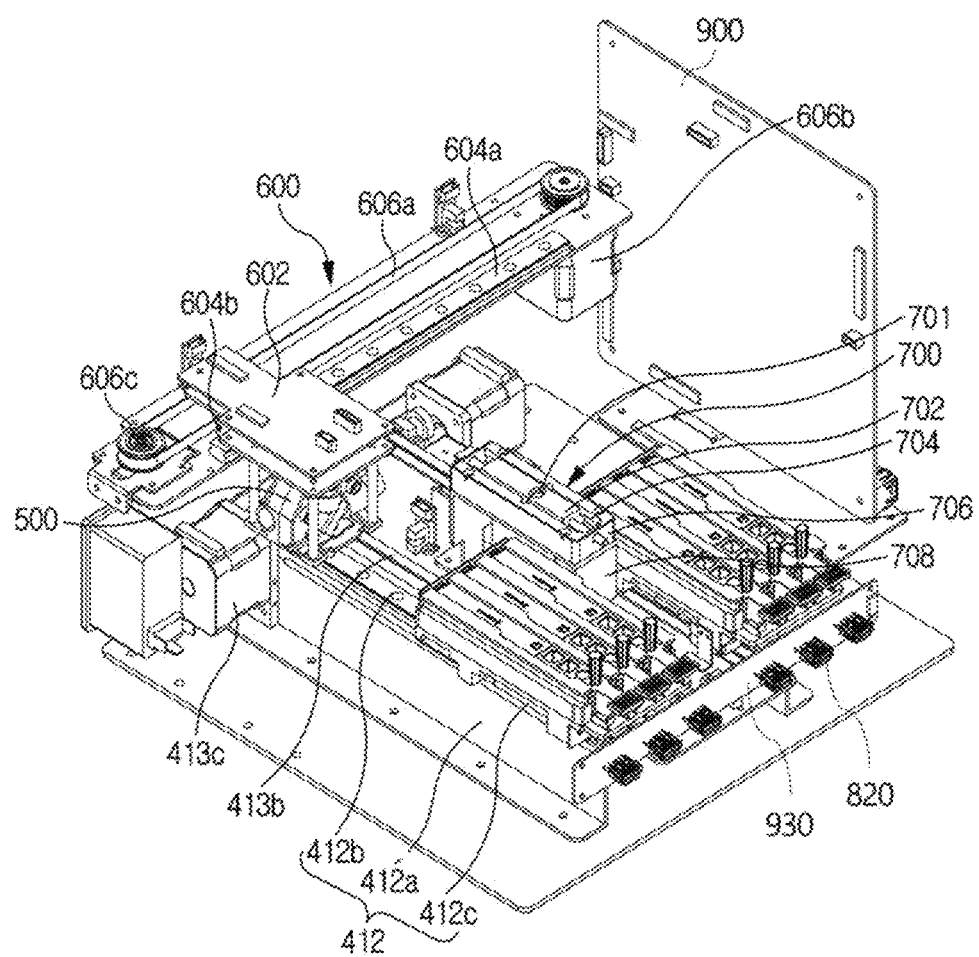
FIG. 5B is a perspective view schematically showing the inside of the station of FIG. 2B while omitting a part thereof.
Figure 6:
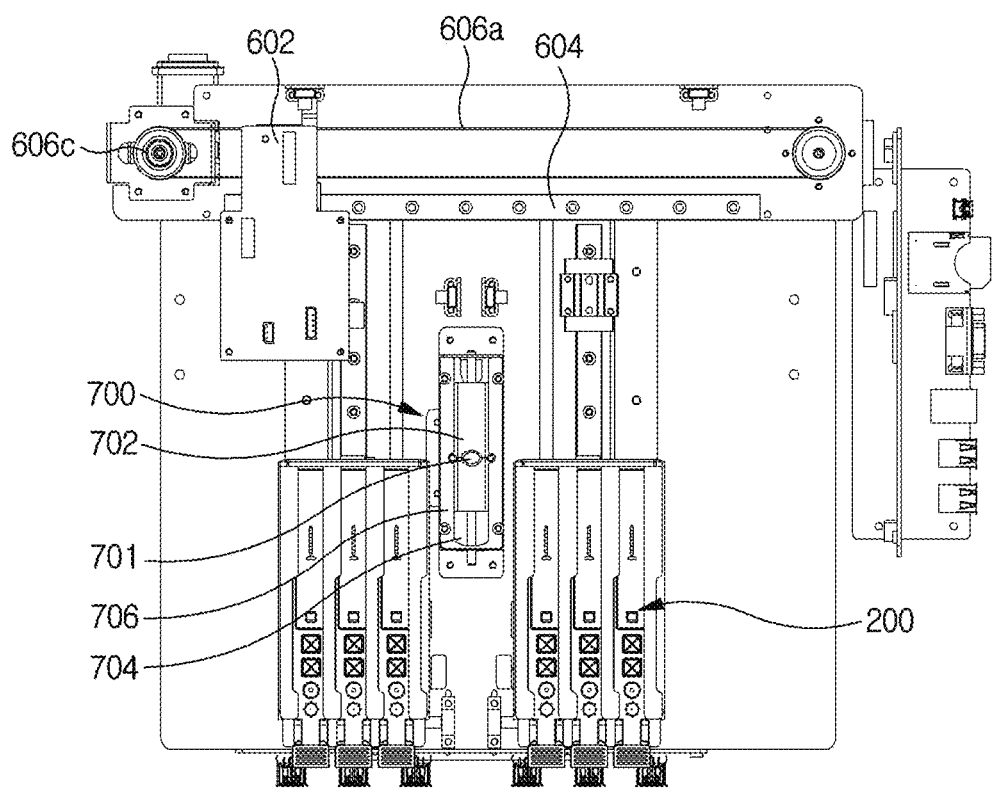
FIG. 6 is a perspective view schematically showing the inside of the station of FIG. 1 in another direction while omitting a part thereof.

FIGS. 2A and 2B through 4 are perspective views schematically showing the inside of the station of FIG. 1 in one direction, and FIGS. 5A, 5B and 6 are perspective views schematically showing the inside of the station of FIG. 1 while omitting a part thereof.

In addition, FIGS. 7 to 12 are perspective views schematically showing the essential elements of driving units in the station shown in FIG. 1, and an optical system or an optical reader.

The station according to the present disclosure is used together with a testing device (e.g., a cuvette) comprising an integrated reaction and detection means. In the present disclosure, the term "station" is used to refer an analyzing system or apparatus for analyzing biological fluid. A cuvette that is used in the station according to the present disclosure is used in detection of an analyte contained in the sample. For detection, in the cuvette, the reaction between a sample and a reagent may be performed, and an analyte in the reaction product can be detected.

As used herein, the term "detection" means determining the presence or absence or amount of an analyte contained in a sample. The reaction product is developed according to a suitable method as described below, and the result of the development is read in the station according to the present disclosure.

As used herein, the term "testing" is meant to encompass detection, analysis and reading.

As used herein, the term "sample" refers to a substance containing either a substance to be analyzed or an analyte, which needs to be detected. A sample that may be used in the present disclosure is a liquid-state or liquid-like flowable material. In one embodiment of the present disclosure, the sample may be a biological sample from a body, such as whole blood, plasma, serum, urine, saliva, feces or a cell extract.

As used herein, the term "analyte" refers to a material to be analyzed in a sample, is also referred to as a marker, and is intended to include proteins and nucleic acids. The proteins include natural or synthetic polypeptides and peptides, and the nucleic acids include natural or synthetic DNA, RNA and cDNA.

As used herein, the term "reagent" is a substance for detection or analysis of the above-described analyte. The kind of reagents varies depending on the kind of specific analyte. For example, the reagent may be either a specific antibody that reacts with various substances (e.g., antigen, etc.) in the above-described biological sample, or an antigen that reacts with an antibody, but is not limited thereto.

A station according to an embodiment of the present disclosure is a station for use with a cuvette 200 which comprises a reaction part comprising a sample collection member standby chamber 210 in which a sample collection member 100 is placed, a sample chamber 220 and a reagent chamber 230, and a detection part 240. The cuvette is inserted into the present station for testing. The station comprises a housing 300, a first driving unit 400, an optical reader 500, a second driving unit 600, and a removal unit 700.

As shown in FIG. 1, the housing 300 that is included in the station according to the present disclosure provides a cover for the station, and also functions to prevent contamination from outside. Particularly, the housing 300 includes an input/output part through which the cuvette 200 is inserted or removed. When the cuvette 200 is inserted into the housing 300 through the input/output part, foreign matter can be prevented from entering the sample chamber 220, reagent chamber 230 and detection part 240 of the cuvette 220 through the housing 300, and thus more accurate testing of the sample can be performed.

Figure 2A:
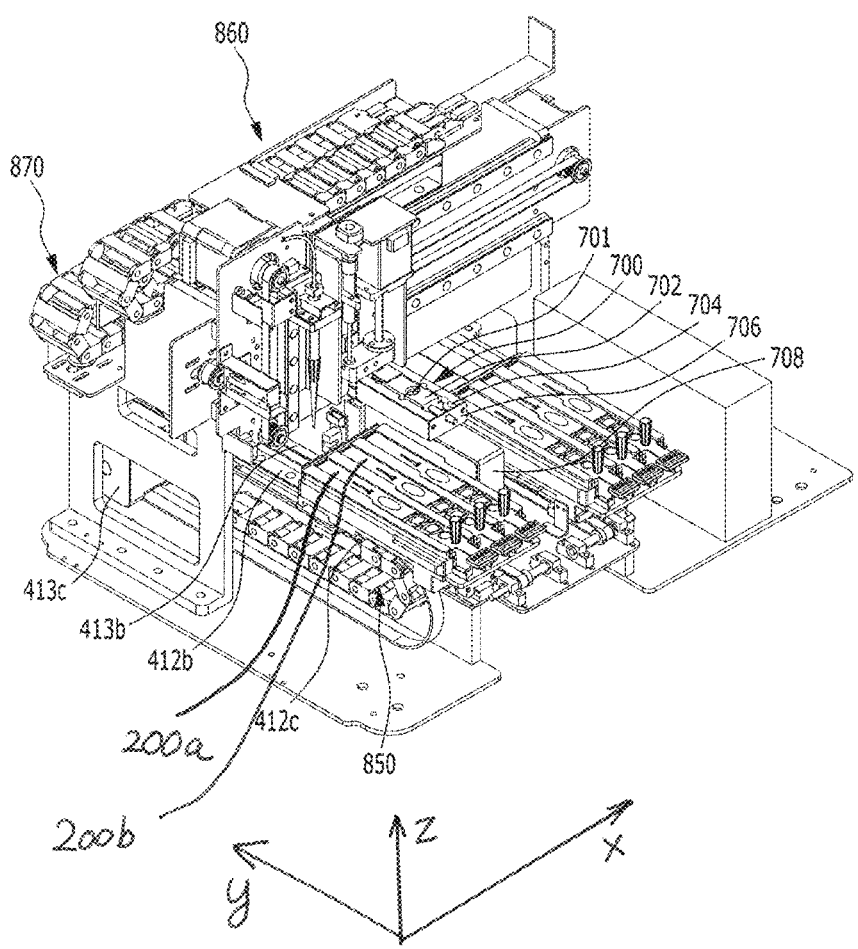
FIG. 2A is a perspective view schematically showing the inside of the station of FIG. 1A in one direction.
Figure 2B:
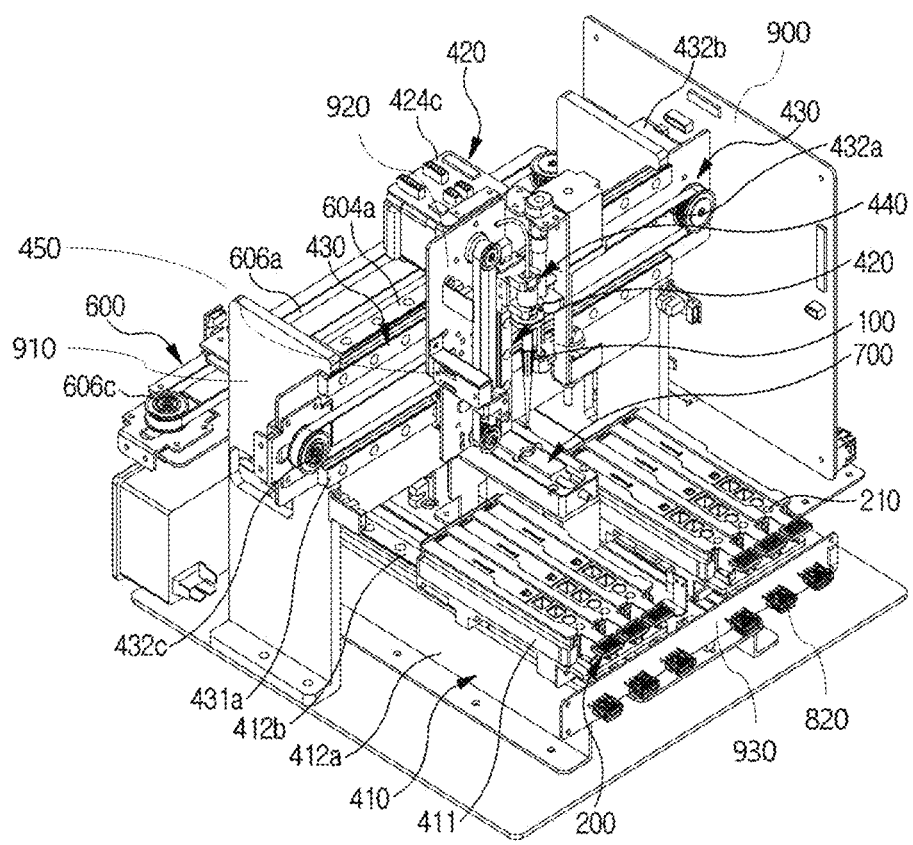
FIG. 2B is a perspective view schematically showing the inside of the station of FIG. 1B in one direction.
Figure 3:
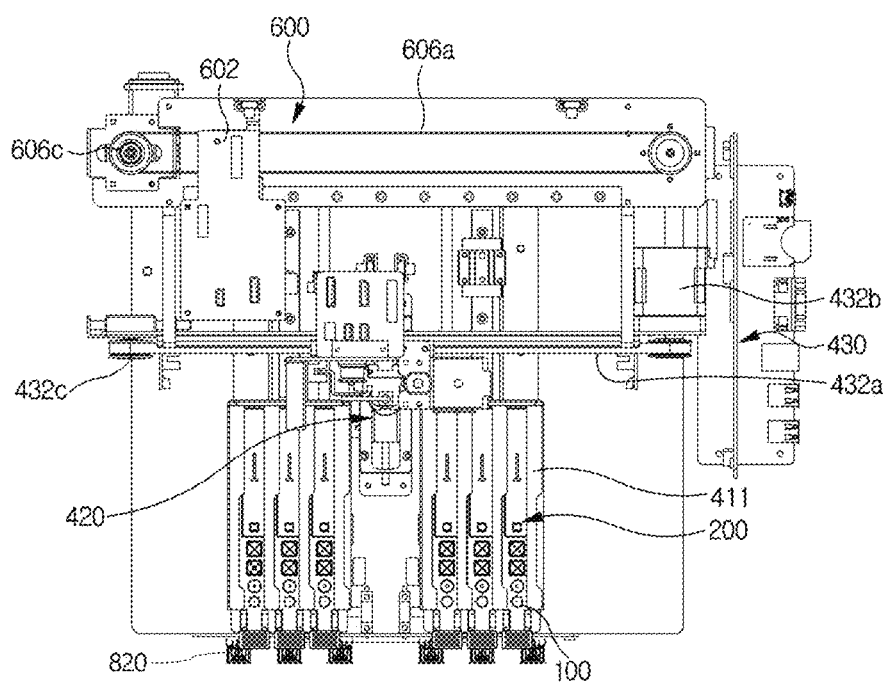
FIG. 3 is a perspective view schematically showing the inside of the station of FIG. 1 in another direction.

As shown in FIGS. 2A and 2B, the first driving unit 400 is included in the housing 300, and is configured to move the mounted cuvette 200 longitudinally, move an arm 423 from one cuvette to another cuvette, allow the sample of the sample chamber 220 to react with the reagent of the reagent chamber 230 while moving the mounted sample collection member 100 vertically, and to inject the reaction product into the detection part 240. The first driving unit is automatically operated by a control unit.

Figure 9:
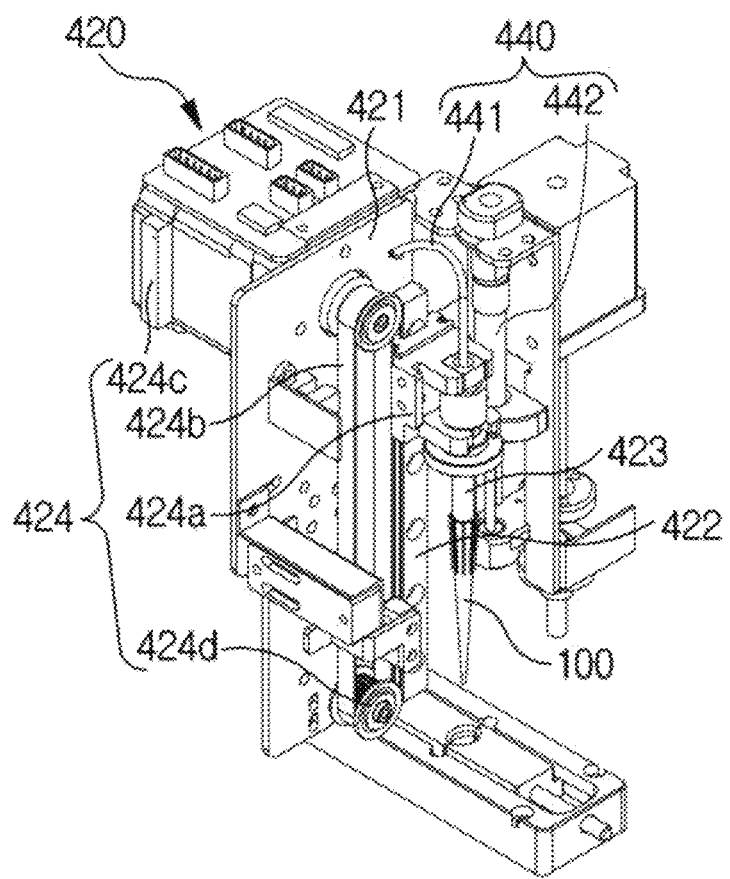
FIG. 9 is a perspective view schematically showing the essential elements of a first driving unit in the station shown in FIG. 1.

As shown in FIG. 9, the sample collection member 100 that is used together with the first driving unit 400 according to the present disclosure may have a tubular shape whose diameter decreases gradually toward the tip so as to be pointed at the tip. Meanwhile, as described herein below, the sample collection member 100 may be made of a flexible material so that it can be easily fixed to the arm 423 and easily separated from the arm 423.

The sample collection member 100 comprises a disposable microtip (e.g., a 2 to 1000 µl micropipette tip), which is locked with the arm 423 as described below and used for distribution or dispensing of the sample and/or the reagent, and it may be used with a system which does not comprise a separate reagent supply device and a means for washing out contaminants. Thus, operation of the system is simplified. Particularly, the sample collection member 100 is mounted in the standby chamber 210 of the cuvette 200 (see FIG. 13), and in this state, when a testing process is started, the sample collection member is locked with the arm 423 as described below (see FIG. 15) and acts together with a pump unit 440 as described below to collect or discharge the sample or the reagent for distribution or dispensing.

Figure 21A:
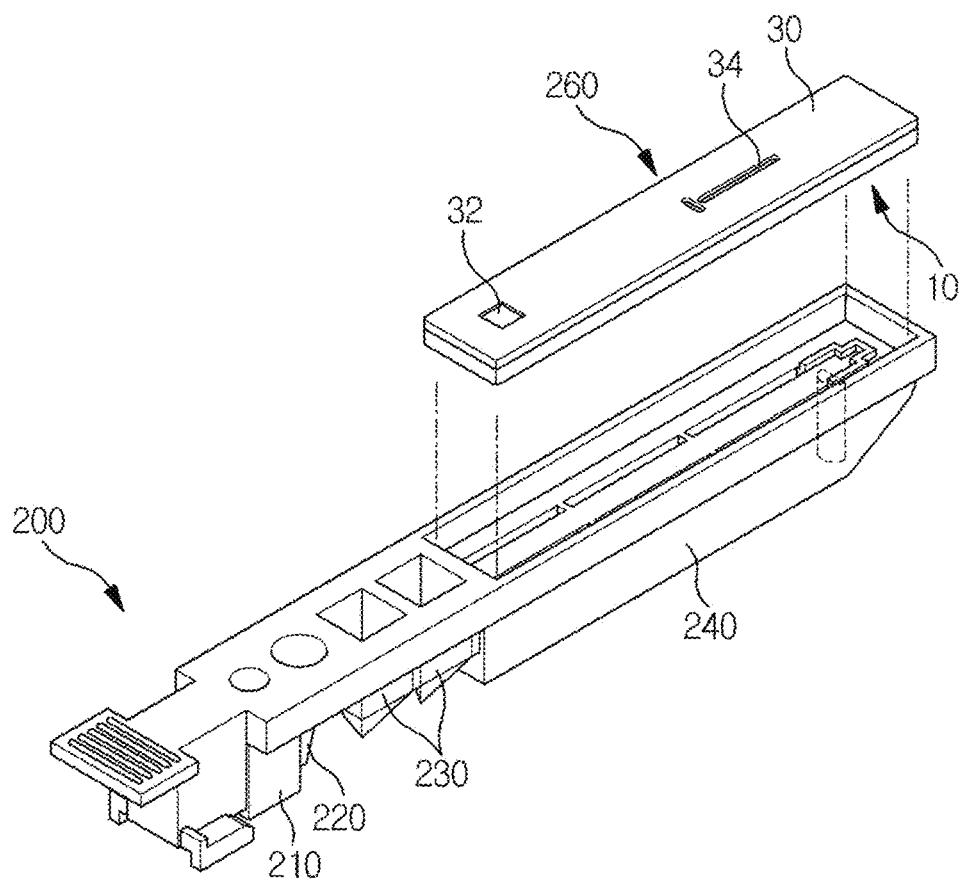
FIGS. 21A and 21B are perspective views showing a cuvette for which the station according to the present disclosure is used, and a detection means which is mounted and used in the cuvette.
Figure 21B:
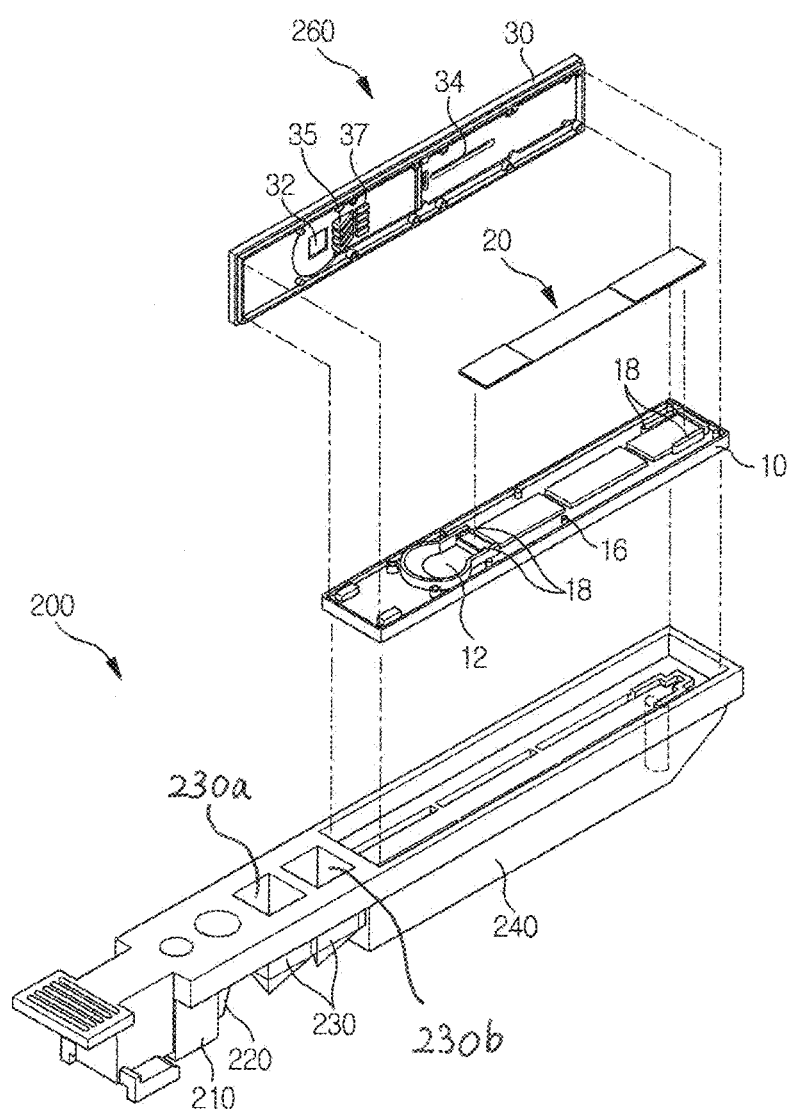

As shown in FIGS. 21A and 21B in one embodiment, the cuvette 200 that is used in the station according to the present disclosure has a long shape, and comprises a standby chamber 210 for collection member, a sample chamber 220, a reagent chamber 230 and a detection part 240. The cuvette 200 according to the present disclosure may be present in plurality. Particularly, the standby chamber 210, the sample chamber 220, the reagent chamber 230 and the detection part 240 may be sequentially arranged along the longitudinal direction of the cuvette 200 so that a testing process can be performed sequentially as the sample collection member 100 linearly moves along the length of the cuvette. The standby chamber 210 is a place in which the sample collection member 100 is placed on standby until a testing process is started; the sample filling chamber 220 is a place in which a specific biological sample containing an analyte to be tested is filled; a reagent chamber 230 is a place in which a reagent such as an antibody or the like, which is to react with the sample, is filled; and the detection part 240 is a place comprising a detection means of lateral flow assay type for detecting a reaction product produced by the reaction between the sample and the reagent.

In one embodiment of the present disclosure, the cuvette 200 may further comprise a barcode or a QR code, which is used interlocked with a chip described below, which is inserted in the station of the present disclosure. In the present disclosure, the barcode comprises UPC-A, UPC-E, EAN, Code 3 of 9, Interleaved 2 of 5, Code 128, UCC/EAN-128, Codabar, PostNet, Pharmacode, or PDF-417, but is not limited thereto, or comprises a 1D barcode or a 2D barcode, but is not limited thereto. The barcode or the QR code encodes both the kind of analyte depending on the kind of sample, and the lot number of the cuvette.

Furthermore, the detection part 240 of the cuvette 200 may comprise a means for detecting a reaction product, particularly a chromatographic analysis means such as a cartridge 260 suitable for lateral flow analysis as shown in FIGS. 21A and 21B. The lateral flow analysis is a method of quantitatively or qualitatively analyzing a target analyte contained in a sample, for example, a specific nucleic acid or protein. Specifically, the lateral flow analysis is a chromatographic method comprising the use of a nitrocellulose membrane (developing membrane), called a strip, in which either an oligonucleotide hybridizing to a nucleic acid having a specific sequence or a specific antibody and/or antigen is bound to a specific position. In this method, an analyte in the reaction product is transferred to the membrane, so that a specific nucleic acid or protein in the sample can be detected through a sequence-specific hybridization reaction or an antigen-antibody reaction. For example, reference may be made to the disclosures of Korean Unexamined Patent Application Publication Nos. 2003-0065341, 2011-0007699 and 2011-0127386, and Korean Patent No. 1149357.

In one embodiment of the present disclosure, a cartridge for lateral flow-type chromatographic analysis, which is provided and used in the detection part 240 of the present disclosure, is as shown in FIGS. 21A and 21B. As shown therein, the cartridge comprises a cover member 30 and a base member 10. A reaction product is introduced into a well 12 through an input part 32. For transfer of the reaction from the well to a strip 20, capillary structures 35 and 37 having a triangular shape are formed on the lower surface of the cover member 30, and structures corresponding thereto are formed on the base member 10. Specifically, the cartridge for lateral flow analysis, which is included in the cuvette 200 according to the present disclosure, comprises a base member 10, and a cover member 30 which is locked with the base member 10, wherein the base member 10 comprises a strip receiving part 18 configured to accommodate a strip used for lateral flow analysis, and a sample well 12 formed at a position extending from one end of the strip receiving part 18. The cover member 30 comprises: a measurement window 34 formed at a portion corresponding to the strip receiving part 18 and configured to detect a reaction product when lacked with the base member 10; and a sample input part 32 formed at a portion corresponding to the sample well 12. If necessary, the cover member may further comprise an air window 38. The base member 10 or the cover member 30, or the base member 10 and the cover member 30, comprise capillary structures 35 and 37. The capillary structures in the cover member 30 are formed on the lower surface so as to be adjacent to the sample input part 32 of the cover member 30, and the capillary structures in the base member 10 are formed in the sample well 12. The sample input part 32 is formed perpendicular to a well that receives the reaction product. When the base member 10 is covered with the cover member 30, they are interlocked with each other at the interface thereof through locking means, including an uneven stopper 16, and thus the cartridge becomes waterproof or sealed aerosol proof. In addition, the strip receiving part 18 comprises a guide for receiving a plurality of strips, which serves to prevent the mounted strips from vibration and to allow the strips to be positioned in place. The reaction product introduced into the input part 32 moves to the strip 20 in various ways. As an example, the lateral flow cartridge may have a specific microchannel structure formed between the well formed perpendicular to the input part and the strip receiving part 18, and through the microchannel structure, the reaction product in the well is transferred to the strip by a capillary phenomenon, and lateral flow is initiated, but the scope of the present disclosure is not limited thereto. As another example, one end of the strip comes into direct contact with the well so that a liquid sample is absorbed into the strip to initiate lateral flow, but the scope of the present disclosure is not limited thereto.

An optical reader or optical system 500 that is included in the station of the present disclosure is provided on the path of left-and-right movement of the cuvette 200, and serves to produce data by reading a reaction product detected using the above-described cuvette 200 and qualify and/or quantify a specific target analyte contained in the sample based on the produced data. To this end, a target analyte or a reagent for detecting the analyte may be labeled with one or more fluorescent substances that emit light at a specific wavelength, and the optical reader 500 is optimized to irradiate light at a specific wavelength depending on the kind of fluorescent substance and to read the light emitted from the fluorescent substance or measure the absorbance of the light. Particularly, in one embodiment of the present disclosure, the optical reader 500 is provided on the path of longitudinal movement of the cuvette 200 and is also movable in a lateral direction in each row of parallel cuvettes. Thus, two or more optical systems may be provided, and analysis of several cuvettes can be performed in a rapid and simple manner.

Meanwhile, the optical system or optical reader 500 may have one or more light sources. If it has two or more light sources, the light sources may produce light with different wavelengths. In addition, fluorescences with different wavelengths may be measured separately, or the absorbances thereof may be measured. Thus, the range of application to diagnostic testing methods can widen, and sensitivity can further increase.

Figure 12:
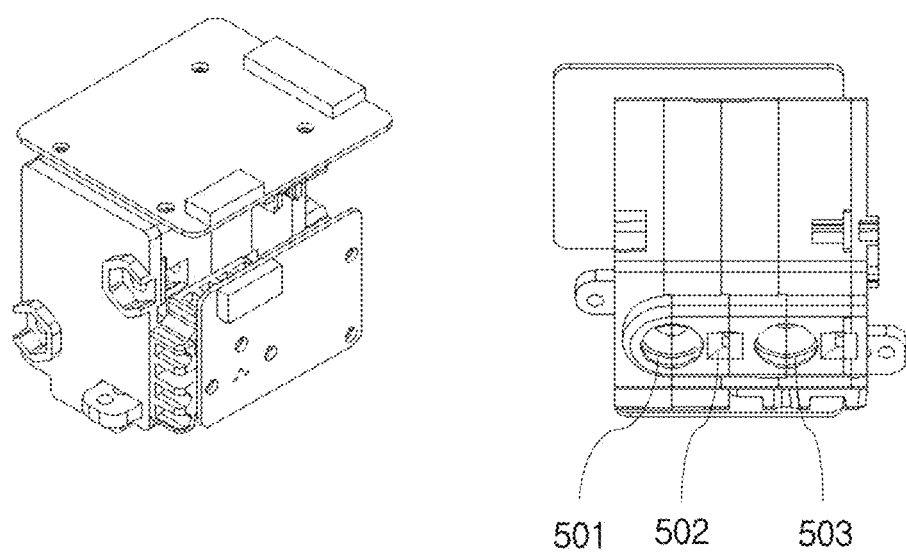
FIG. 12 is a perspective view schematically showing an optical reader extracted from the station shown in FIG. 2A.

As shown in FIG. 12, the optical reader 500 according to the present disclosure may comprise a first fluorescent measurement part 501, a second fluorescent measurement part 503, and an absorbance measurement part 502, and each of the fluorescent measurement parts may comprise an LED light source or a laser light source.

As shown in FIGS. 2A, 2B and 6, the optical reader 500 according to the present disclosure may be moved laterally by a second driving unit 600 provided in the housing 300 so that the optical reader 500 may be positioned over any one of a plurality of cuvettes 200 to perform analysis of a sample in the corresponding cuvette 200. The second driving unit 600 is automatically driven by a control unit.

The first driving unit 400 as described above will now be described in further detail with reference to FIGS. 2A and 2B through 9.

As shown in FIGS. 2A and 2B, the first driving unit 400 may comprise: a longitudinal moving unit 410 configured to move the cuvette 200 forward and backward (forward and/or backward, or along the Y-axis); a vertical moving unit 420 configured to move the sample collection member 100 vertically (upward and/or downward, or along the Z-axis) for sample suction, sample/reagent mixing, and dropping of a reaction product; a laterally moving unit 430 (left and/or right, or along the X-axis); and a pump unit 440 configured to provide a suction force or a discharge force to the sample collection member 100.

First, the frontward and backward moving unit 410 will be described with reference to FIGS. 2A and 2B through 8.

The frontward and backward moving unit 410 serves to position any one of the sample chamber 220, the reagent chamber 230 and the detection part 240 at a point at which the sample collection member 100 is positioned, while moving the cuvette 200 forward and backward. For example, as shown in FIGS. 2A and 2B through 6, the longitudinal moving unit 410 may comprise a holder 411, a longitudinal guiding part 412, and a longitudinal driving part 413.

As shown in FIGS. 1, 2A and 2B, the holder 411 is provided at a position corresponding to the input/output part of the housing 300, and the cuvette 200 is seated therein. For example, when the cuvette 200 is inserted and pushed into the holder 411 through the input/output part (see FIG. 13), the cuvette 200 is completely inserted and seated in the holder 411 (see FIGS. 2A and 2B).

Figure 7A:
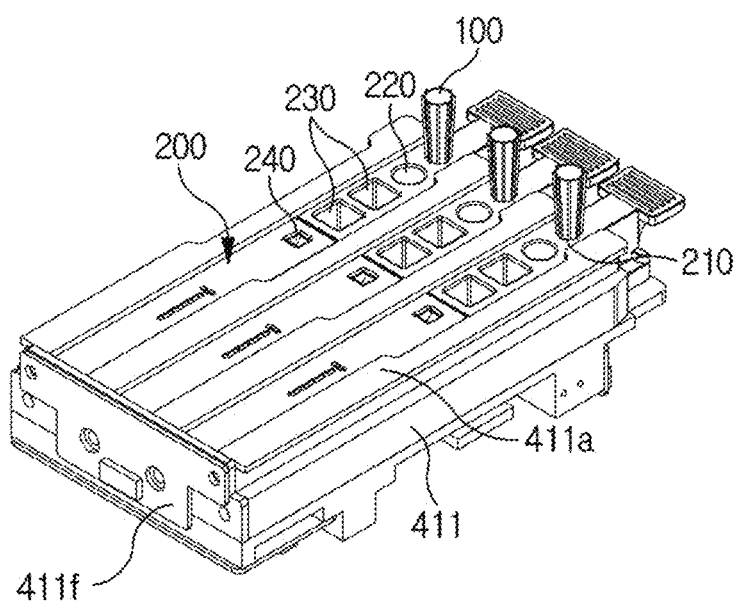
FIG. 7A is a perspective view schematically showing a holder extracted from the station of FIG. 1.
Figure 7B:
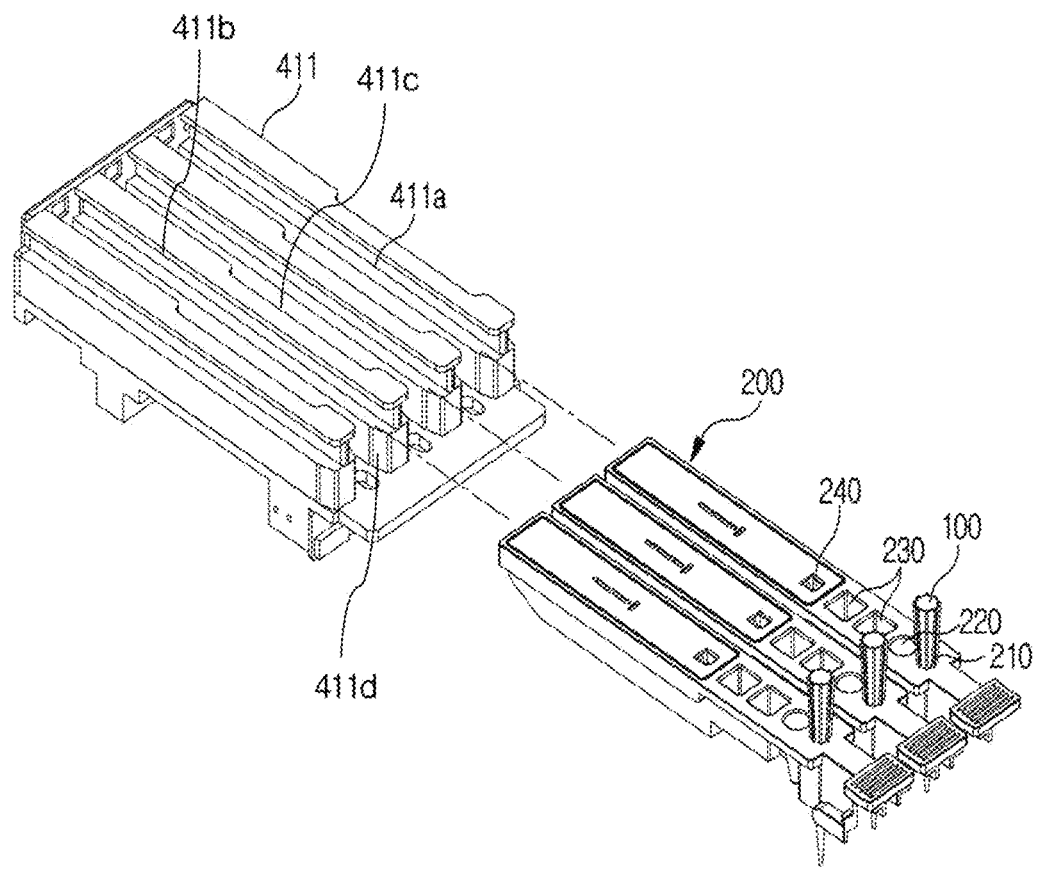
FIG. 7B is a perspective view showing the coupling between a holder and cuvette in the station of FIG. 1.
Figure 7C:
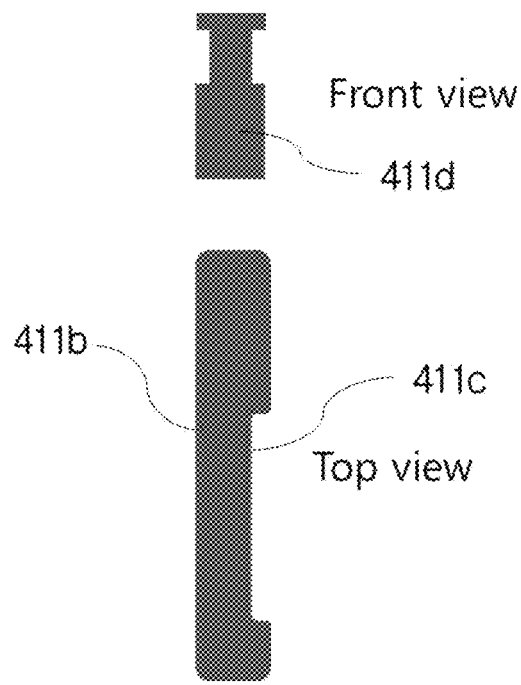
FIG. 7C shows a front view and a top view of a cuvette-fixing member provided in the holder of FIG. 7B.

Meanwhile, as shown in FIGS. 7B and 7C, the holder 411 has formed therein one or more cuvette mounting channels 411a so that one or more cuvettes 200 may be inserted and mounted therein. The channels are isolated from each other by specific walls 411d, and flange-type cuvette fixing members 411b and 411c having an asymmetric lateral shape are formed on the upper side of each wall forming the boundary between the channels. As shown in FIGS. 7A and 7B, a plurality of slot-type mounting channels 411a are formed in the holder 411. In the upper portion of each mounting channel 411a, protrusion-type fixing members 411b and 411c are formed along the lengthwise direction of each channel in order to fix the cuvette inserted in the mounting channel. One side of the fixing member is asymmetric to the other side. Specifically, one side of the fixing member has a linear shape, and the other side has a partially recessed shape 411c. The fixing member makes it possible to securely mount the cuvette 200 inserted in the channel without vibration and also makes it possible to read the barcode formed on the upper side of the cuvette. The holder 411 may have a plurality of channels, and thus examination of a plurality of cuvettes may be performed, but it is not necessary that the cuvette is mounted in all the channels. In this case, the plurality of mounting channels 411a may be formed in parallel in a lateral direction so that the plurality of cuvettes 200 can be inserted therein so as to be arranged in parallel in a lateral direction.

The longitudinal guiding part 412 serves to guide the holder 411 forward and backward. For example, as shown in FIGS. 2A, 2B, 5A and 5B, the longitudinal guiding part 412 may comprise a horizontal support 412a, a longitudinal guiding rail 412b, and a longitudinal guiding groove 412c. As shown in FIGS. 2A and 2B, the horizontal support 412a is provided between the housing 300 and the holder 411 and serves to support the holder 411 in the housing 300. As shown in FIGS. 2A, 2B and 5, the longitudinal guiding rail 412b may be formed to protrude at a portion of the horizontal support 412a, which contacts with the holder 411. In embodiments, the longitudinal guiding rail 412b may also be formed at a portion of the holder 411, which contacts with the horizontal support 412a. As shown in FIGS. 2A, 2B and 5, the longitudinal guiding groove 412c may be formed at a portion of the holder 411, which contacts with the horizontal support 412a, so as to engage the longitudinal guiding rail 412b, when the guiding rail 412b is formed on the horizontal support 412a. In embodiments, the longitudinal guiding groove 412c may also be formed at a portion of the horizontal support 412a, which contacts with the holder 411, so as to engage the longitudinal guiding rail 412b. Thus, the holder 411 can be guided left and right through the longitudinal guiding part 412 without vibration.

The longitudinal driving part 413 serves to apply a longitudinal force to the holder 411. For example, as shown in FIGS. 2A, 2B, 5A and 5B, it may comprise a first connecting bracket 413a, a first belt 413b, a first motor 413c, and a first driven pulley 413d. The first connecting bracket 413a connects the holder 411 and the first belt 413b to each other. The first belt 413b is fixed to the first connecting bracket 413a and serves to transfer the power of the first motor 413c to the first connecting bracket 413a. The first motor 413c is provided on one side of the first belt 413b and serves to rotate the first belt 413b. The first driven pulley 413d is provided on the other side of the first belt 413b and rotatably supports the first belt 413b. In particular, the pulley-belt type longitudinal driving part 413 is provided, and thus can prevent vibration and foreign matter from being caused by friction during lateral movement, unlike a gear type, so that more accurate testing can be achieved.

Figure 7E:
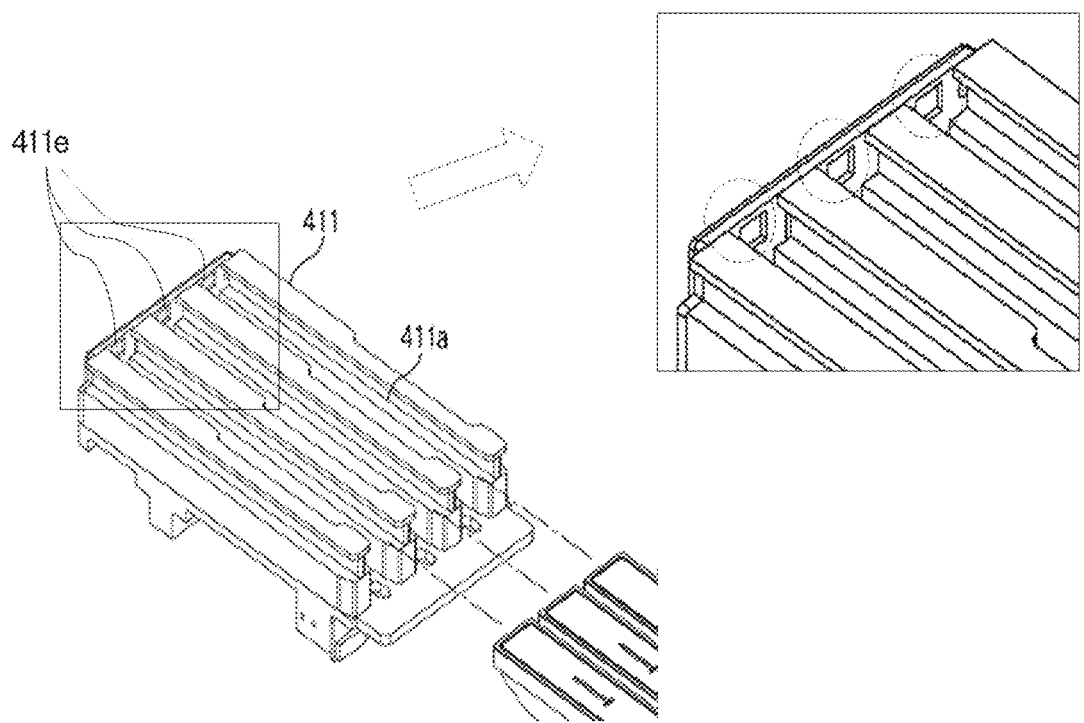
FIG. 7E depicts a perspective view schematically showing a sensor (attached to the backside of the holder) for sensing whether a cuvette would be mounted, and also depicts a partially enlarged view of the sensor.
Figure 8:
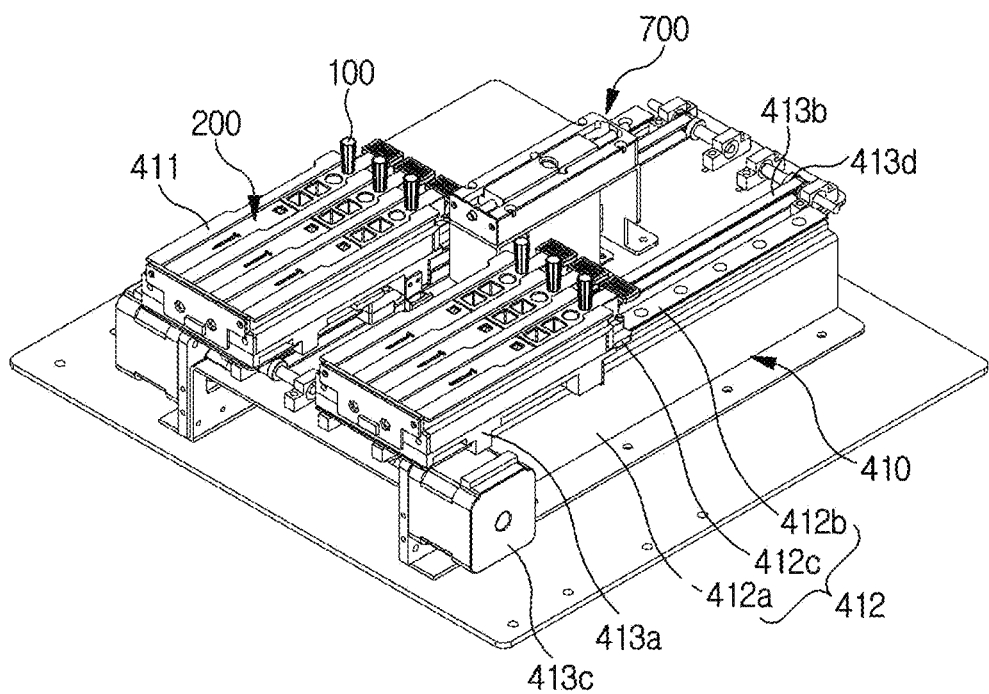
FIG. 8 is a perspective view schematically showing the essential elements of a first driving unit in the station shown in FIG. 1.

Meanwhile, the longitudinal moving unit 410 may be provided in plurality. Namely, as shown in FIGS. 2A, 2B, 5A and 5B, two longitudinal moving units 410 may be arranged in parallel in a lateral direction. Meanwhile, the number of the longitudinal moving units 410 is not limited thereto. Herein, "longitudinal moving unit 410 is provided in plurality" means that each of the above-described holder 411, longitudinal guiding part 412 and longitudinal driving part 413 is provided in plurality. In this case, the direction of movement of the plurality of longitudinal moving units 410 is a longitudinal direction, and these units move in parallel. Accordingly, cuvettes 200 having different kinds of samples can be tested at the same time, and thus the time required for analysis is reduced and the convenience of analysis is increased. For example, as shown in FIGS. 7 and 8, two holders 411, each having three mounting channels, may be provided, and thus a total of six cuvettes 200 may be performed at the same time, but the number thereof is not limited thereto. Meanwhile, the longitudinal moving units 410 may be driven independently of each other so that testing may be more easily performed. Namely, as shown in the figures, even when the longitudinal moving units 410 are two in number, they may be driven independently of each other so that each cuvette provided in each unit can be independently tested.

Meanwhile, a removal unit 700 may further be provided which is disposed between the plurality of longitudinal moving units 410 and which serves to separate the sample collection member 100 from the vertical moving unit 420. After the use of the sample collection member 100, the removal unit 700 serves to separate the used sample collection member 100 from the vertical moving unit 420 in order to connect a fresh sample collection member 100 to the vertical moving unit 420.

Figure 19A:
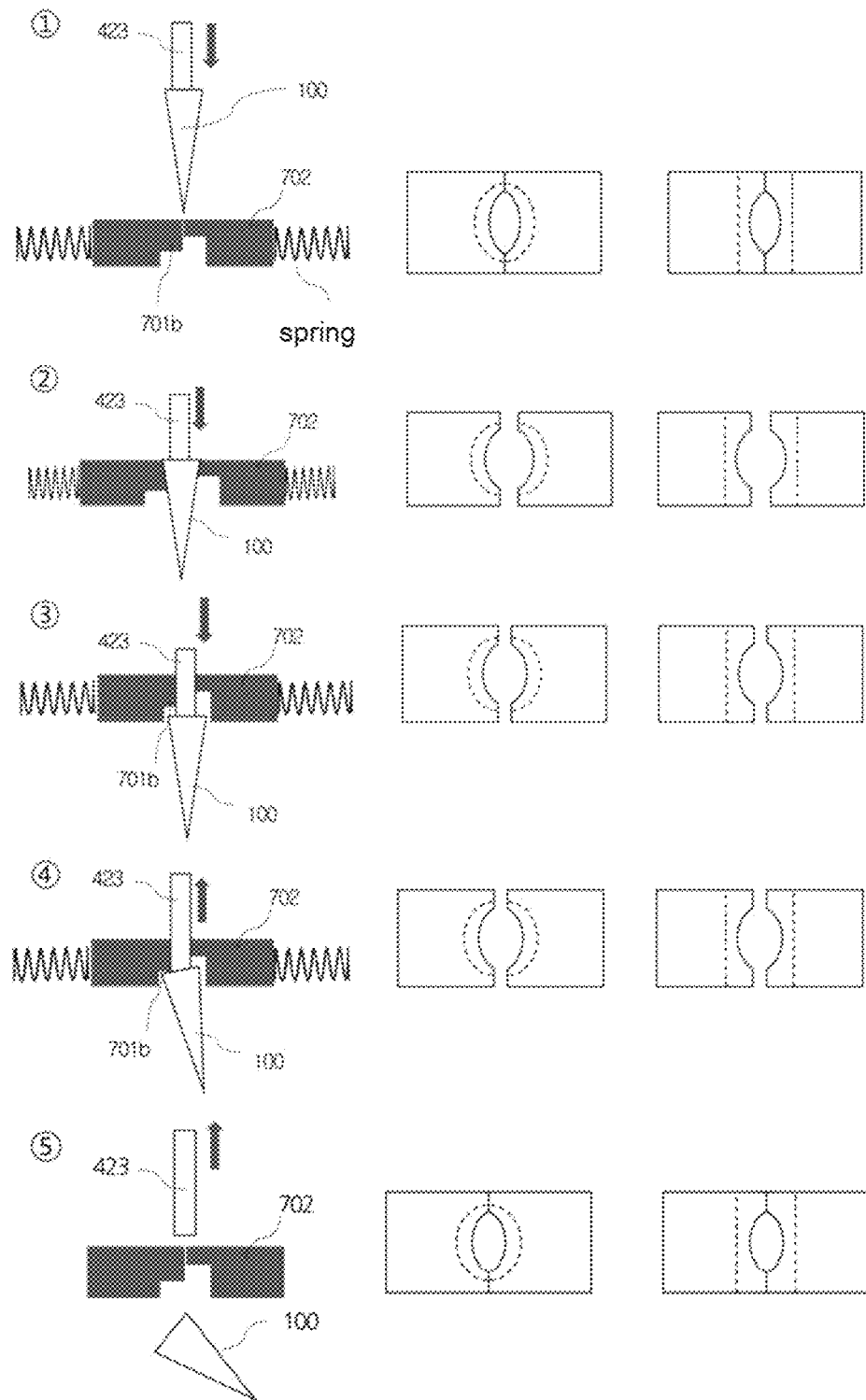
FIGS. 19A and 19B schematically show a process in which a sample collection member is separated by the sample collection member removal unit shown in FIGS. 17 and 18, and the size relationship between the inner groove of a hole and the outer diameter of the sample collection member, respectively.
Figure 19B:
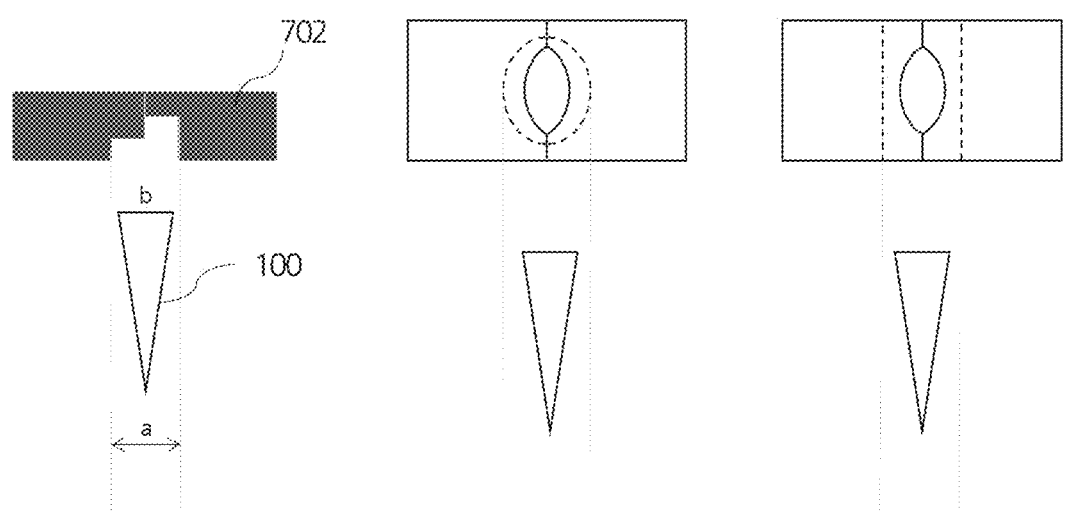

The removal unit 700 will now be described with reference to FIGS. 2A, 2B, 5A, 5B, 6, 19A and 19B. The removal unit 700 may comprise a slider 702 which is slidably movable in one direction and which has a vertical through-hole 701. The slider 702 is configured to be slidably movable in one direction, and has a vertical through-hole 701. When the sample collection member 100 is inserted into the through-hole 701, the slider 702 moves in a sliding manner so that the size of the through-hole can be controlled depending on the cross-sectional diameter of the inserted tip and arm. Thus, as shown in FIG. 19A, when the sample collection member 100 is inserted (①, ② and ③) and pushed upward (④ and ⑤), the inserted sample collection member at the end of the arm gets caught by a removal stopper 701b formed at the edge of the lower side of the through-hole ((④)) so that it can be separated from the arm ((⑤)). In embodiments, as shown in 19B, the outer diameter "a" of the groove formed in the lower side of the through-hole is larger than the outer diameter b of the sample collection member.

The removal unit 700 is positioned on a path along which the sample collection member 100 is moved laterally by the first laterally moving unit 430. Accordingly, when the use of the sample collection member 100 is completed, the sample collection member 100 may be positioned on the removal unit 700 using the first laterally moving unit 430, and then separated by insertion into the through-hole 701. As shown in FIG. 19A, on the lower side of the removal unit 700 in which the through-hole 701 is located, a groove is formed along the edge of the through-hole, and a stopper 701b for facilitating separation of the sample collection member 100 is formed in a portion of the groove. The stopper 701b is formed only in a portion of the left or right side of the groove formed on the lower side of the through-hole. Thus, when the sample collection member inserted through the through-hole is separated or removed from the vertical moving unit 420, a load is applied only to a portion of the upper edge of the sample collection member, and thus the sample collection member is easily separated. As shown in the right of FIG. 19a, the inside of the groove on the lower side of the through-hole may be formed along the circumference of the through-hole, and the outside of the groove may be formed linearly or along the circumference of the through-hole.

More specifically, the removal unit 700 may further comprise a jig 706 having a sliding hole 704, a waste box 708, and a spring. The jig 706 has a sliding hole 704 which is formed vertically so as to form a path along which the slide 702 moves slidably, in which the sliding hole extends longitudinally. Accordingly, the slider 702 is disposed in the sliding hole 704 formed in the jig 706 and is slidable along the sliding hole 704. The sliding hole 704 is configured such that it extends vertically so that the slider 702 can be exposed in a vertical direction.

The waste box 708 is disposed below the jig 706, and is configured such that the sample collection member 100 separated from the vertical moving unit 420 is dropped into the waste box.

Meanwhile, a spring may further be provided which is disposed in the sliding hole 704 and which serves to apply elasticity between the inner surface of the sliding hole 704 and the slider 702 so as to elastically bias the slider 702. Accordingly, if a separate external force or operating signal is absent, the slider 702 may be maintained on standby at a specific position.

Hereinafter, the vertical moving unit 420 as described above will be described in further detail with reference to FIGS. 4 and 9.

The vertical moving unit 420 is linked with the sample collection member 100 and serves to move the sample collection member 100 upward and downward in and out of any one of the sample chamber 220, reagent chamber 230 and lateral flow type chromatography-based detection part 240 of the cuvette 200. Thus, the sample collection member 100 may be moved upward and downward by the vertical moving unit 420 and may be inserted into any one chamber or separated from the chamber. For example, as shown in FIGS. 4 and 9, the vertical moving unit 420 may comprise a second connecting bracket 421, a vertical guiding rail 422, an arm 423, and a vertical driving part 424.

The second connecting bracket 421 generally serves as a structure that supports the vertical moving unit 420, and is provided to be connected to a first laterally moving unit 430 as described below.

The vertical guiding rail 422 is provided in the second connecting bracket 421 so as to extend long upward and downward. Particularly, as shown in FIG. 9, where the vertical guiding rail 422 has a protruding shape, a groove corresponding thereto is formed either on one side of the arm 423 or on a third connecting bracket 424a connected to the arm 423.

The arm 423 is moved vertically along the vertical guiding rail 422. When sample testing is started, the sample collection member 100 is automatically bound to the end of the arm 423 by the longitudinal moving unit 410 and the vertical moving unit 420. The arm serves to bind the sample collection member so as to prevent internal pressure from being removed. In addition, in order to increase adhesion to the surface of a hard material, a portion of the arm, which binds to the sample collection member, may be covered with a highly adhesive material, for example, a urethane-based rubber material.

The vertical driving part 424 serves to apply a force in a vertical direction to the arm 423. For example, as shown in FIGS. 4 and 9, it may comprise a third connecting bracket 424a, a second belt 424b, a second motor 424c, and a second driven pulley 424d.

The third connecting bracket 424a is connected to the arm 423, and one side thereof is connected to the vertical guiding rail 422, and the other side is connected to a second belt 424b as described below. In a portion of the third connecting bracket 424a, which is connected to the vertical guiding rail 422, a groove corresponding thereto is formed so that the third connecting bracket 424a is guided by the vertical guiding rail 422.

The second belt 424b extends long vertically, and is fixed to the third connecting bracket 424a so as to transfer the power of the second motor 424c to the third connecting bracket 424a. The second motor 424c is provided on one side of the second belt 424b and serves to rotate the belt 424b. The second driven pulley 424d is provided on the other side of the second belt 424b and serves to rotatably support the second belt 424b. In particular, the pulley-belt type longitudinal driving part 424 is provided which can prevent vibration and foreign matter from being caused by friction during lateral movement, unlike a gear type, so that more accurate testing can be achieved. Furthermore, lateral vibration of the arm 423 during vertical movement can be prevented, and thus the sample collection member 100 can be accurately moved vertically. In addition, the vertical guiding rail 422 is configured to correspond to the groove, and thus vibration may further be prevented.

Hereinafter, the first laterally moving unit 430 as described above will be described with reference to FIGS. 2 and 10.

The first laterally moving unit 430 is connected to the vertical moving unit 420 and serves to move the vertical moving unit 420 and the sample collection member 100 in lateral directions. Thus, the sample collection member 100 can be moved laterally by the first laterally moving unit 430 and poisoned on any one of the plurality of cuvettes 200 arranged in parallel in a lateral direction. Thus, sample analysis for the one cuvette 200 may be performed.

For example, the first laterally moving unit 430 may comprise: a first laterally guiding part 431 configured to guide the second connecting bracket 421 in left and right directions; and a first laterally driving part 432 configured to apply a force in left and right directions to the second connecting bracket 421.

The first laterally guiding part 431 may comprise: a first laterally guiding rail 431a provided to extend long laterally in the housing 300; and a first laterally guiding part 431b provided in the second connecting bracket 421 and engaging the first laterally guiding rail 431a.

Figure 10:
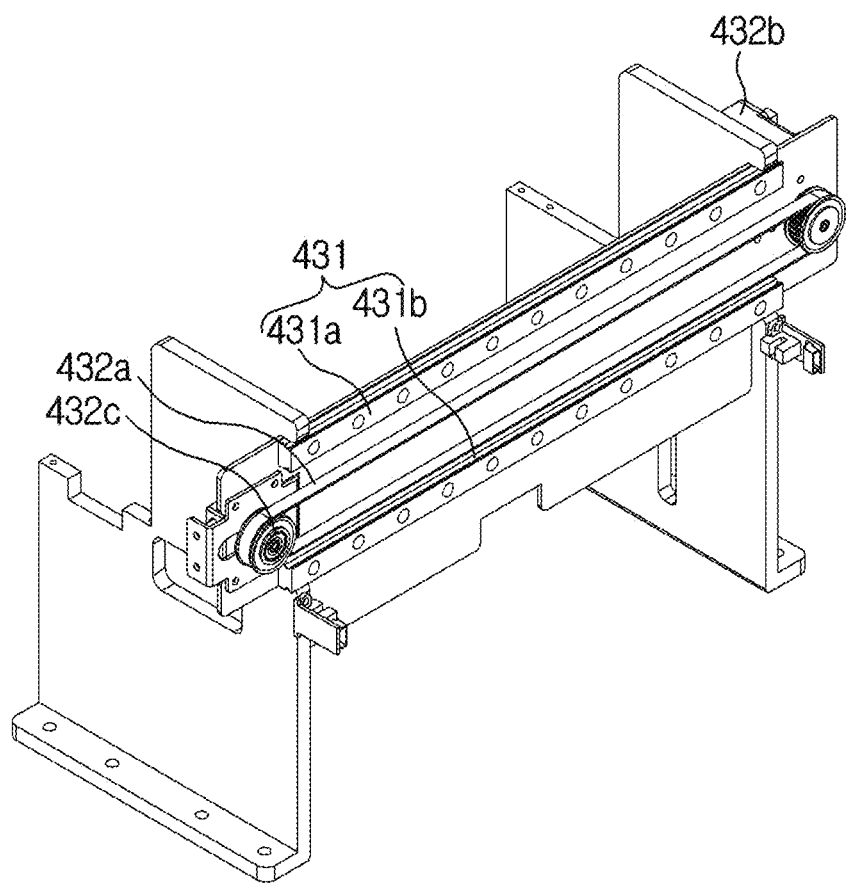
FIG. 10 is a perspective view schematically showing the essential elements of a first driving unit in the station shown in FIG. 1.
Figure 11A:
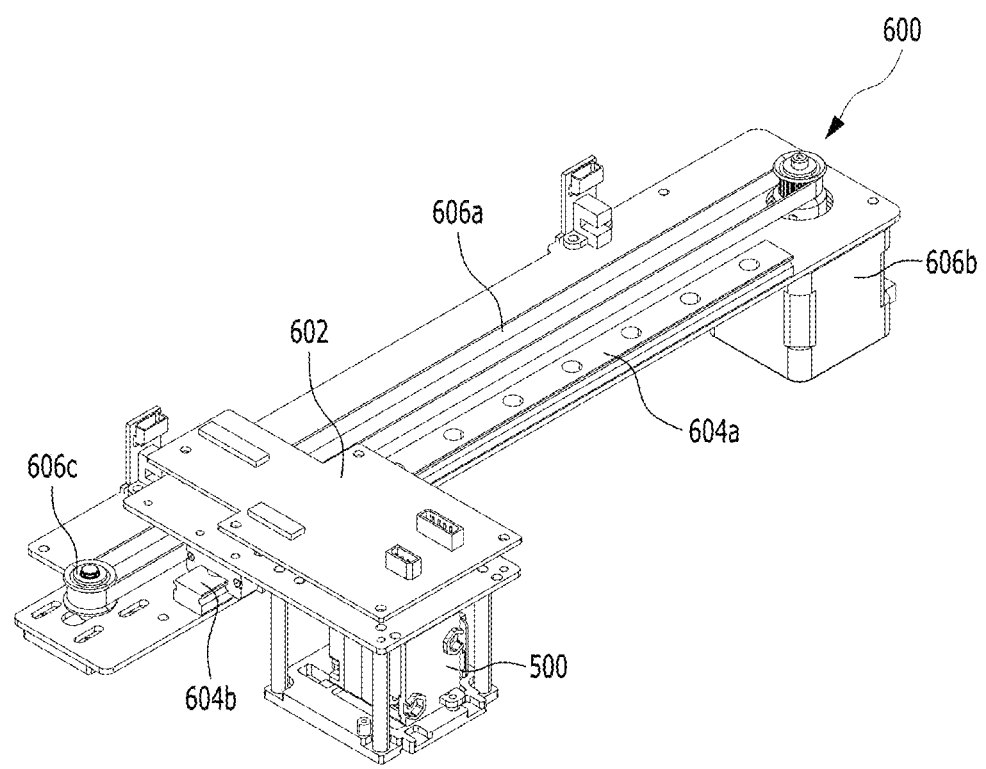
FIG. 11A is a perspective view schematically showing the essential elements of a second driving unit in the station shown in FIG. 2A.
Figure 11B:
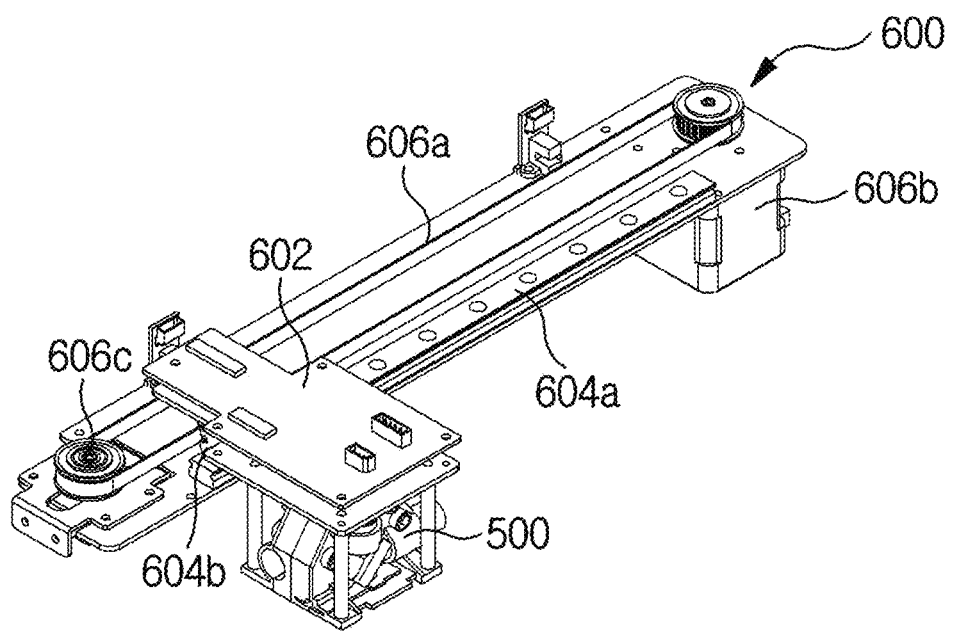
FIG. 11B is a perspective view schematically showing the essential elements of a second driving unit in the station shown in FIG. 2B.

The first laterally guiding rail 431a extends long left and right in the housing and is provided in parallel with the path of left-and-right movement of the second connecting bracket 421. Meanwhile, on both sides of the first laterally guiding rail 431a, specific supporting members may be provided, respectively. Meanwhile, a specific bar-like member is provided which extends between the supporting means so that the first laterally guiding rail 431a is provided, and one or more first laterally guiding rails 431a may be provided on the bar. For example, as shown in FIG. 10, two first laterally guiding rails 431a are provided which extend in parallel while being spaced from each other in a vertical direction.

Corresponding to the first laterally guiding rail 431a, a first laterally guiding part 431b is provided in the second collection bracket 421. The first laterally guiding part 431b comprises a guide groove engaging the first laterally guiding rail 431a, so that the second connecting bracket 421 is movable along the first laterally guiding rail 431a.

The first laterally driving part 432 serves to apply a force in left and right directions to the second connecting bracket 421. For example, as shown in FIGS. 2 and 10, it may comprise a third belt 432a, a third motor 432b, and a third driven pulley 432c. Herein, "applying a force in left and right, or lateral directions to the second connecting bracket 421" may mean applying a force in left and right directions to the sample collection member 100 and the vertical moving unit 420 connected to the second connecting bracket 421 to thereby move them.

The third belt 432a extends long laterally and is fixed to the second connecting bracket 421 so as to transfer the power of the third motor 432b to the second connecting bracket 421. The third motor 432b is provided on one side of the third belt 432a so as to rotate the third belt 432a. The third driven pulley 432c is provided on the other side of the third belt 432a so as to rotatably support the third belt 432a. In particular, the pulley-belt type of the first laterally driving part 432 is provided which can prevent vibration and foreign matter from being caused by friction during lateral movement, unlike a gear type, so that more accurate testing can be achieved. Furthermore, lateral vibration during lateral movement can be prevented, and thus the sample collection member 100 can be accurately moved left and right. In addition, the first laterally guiding rail 431a is configured to correspond to the first laterally guiding part 431b, and thus vibration may further be prevented.

As described above, as the vertical moving unit 420 and the first laterally moving unit 430 are provided, the sample collection member 100 can move upward and downward and left and right. Thus, after the sample collection member 100 is positioned at a position corresponding to any one of the plurality of cuvettes 200 arranged in parallel, testing may be performed.

Hereinafter, the pump unit 440 as described will be described in further detail with reference to FIGS. 4 and 9 again.

The pump unit 440 serves to provide a suction force or a discharge force after the sample collection member 100 is inserted into any one of the sample chamber 220, reagent chamber 230 and detection part 240 of the cuvette 200. Specifically, the pump unit 440 may provide a suction force to the sample collection member 100 (see FIG. 16(a)), after the sample collection member 100 is positioned over a specific cuvette 200 by the laterally moving unit 430 and the sample chamber 220 is positioned under the sample collection member 100 by the longitudinal moving unit 410 and the sample collection member 100 is also inserted into the sample chamber 220 by the vertical moving unit 420. Furthermore, after the reagent chamber 230 is positioned under the sample collection member 100 by the longitudinal moving unit 410 and the sample collection member 100 is inserted into the reagent chamber 230 by the vertical moving unit 420, the pump unit may alternately provide a suction force and a discharge force to the sample collection member 100 (see FIG. 16(b)). In addition, after the detection part 240 is positioned under the sample collection member 100 by the longitudinal moving unit 410 and the sample collection member 100 is inserted into the detection part 240 by the vertical moving unit 420, the pump unit may provide a discharge force to the sample collection member 100 (see FIG. 16(c)).

For example, as shown in FIGS. 4 and 9, the pump unit 440 may comprise a tube line 441 and a pump 442. The tube line 441 is formed to pass through the arm 423 so as to transfer the pumping force of the pump 442 to the sample collection member 100. The pump 442 is a unit connected to the tube line passing through the arm. It provides a pumping force to the sample collection member 100 through the tube line 441. Thus, as the pump unit 440 is provided, the amount of sample, reagent or reaction product sucked or discharged through the sample collection member 100 can be accurately controlled.

Hereinafter, the second driving unit 600 as described above will be described in further detail with reference to FIGS. 5A, 5B, 6, 11A, 11B and 20.

As described above, the second driving unit 600 serves to drive the optical reader 500, and may comprise: a fourth connecting bracket 602 to which the optical reader 500 is connected; a second laterally guiding part 604 configured to guide the fourth connecting bracket 602 in left and right directions; and a second laterally driving part 606 configured to apply a force in left and right directions to the fourth connecting bracket 602.

As used herein, "left and right, or lateral directions" is directions parallel to directions in which the sample collection member 100 is moved by the first laterally moving unit 432 as described above. The left and right directions may be directions in which the plurality of cuvettes 200 are arranged in parallel. Accordingly, the second driving unit 600 may be configured to position the optical reader 500 over any one of the plurality of cuvettes 200 arranged in parallel in lateral directions.

The fourth connecting bracket 602 is a member to which the optical reader 500 is connected and fixed. Furthermore, it is configured to be connected to the second laterally guiding part 604 and the second laterally driving part 606. As shown in FIGS. 5A and 5B, the fourth connecting bracket 602 may be composed of a connection means such as a leg that extends with a specific length.

The structure of the second laterally guiding part 604 is similar to the structure of the first laterally guiding part 431 as described above. Specifically, the second laterally guiding part 604 may comprise: a second laterally guiding rail 604a provided to extend long laterally in the housing 300; and a second laterally guiding part 604b having a second laterally guiding groove which is provided in the fourth connecting bracket 602 and which engages the second laterally guiding rail 604a.

The second laterally guiding rail 604a extends long left and right in the housing 300 and is provided in parallel with a path along which the fourth connecting bracket 602 moves left and right. Meanwhile, on both sides of the second laterally guiding rail 604a, specific supporting members may be provided, respectively. Meanwhile, a specific bar-like member is provided which extends between the supporting members so that the second laterally guiding rail 604a is provided, and the second laterally guiding rail 604a may be provided on the bar.

Corresponding to the second laterally guiding rail 604a, a second laterally guiding part 604b is provided in the fourth collection bracket 602. The second laterally guiding part 604b comprises a laterally guiding groove engaging the second laterally guiding rail 604a, so that the fourth connecting bracket 602 is movable along the second laterally guiding rail 604a.

The second laterally driving part 606 also has a structure similar to that of the first laterally driving part 432. Namely, the second laterally driving part 606 may comprise: a ring-shaped fourth belt 606a to which the fourth connecting bracket 602 is fixed and which extends long laterally; a fourth motor 606b provided on one side of the fourth belt 606a so as to rotate the fourth belt 606a; and a fourth driven pulley 606c provided on the other side of the fourth belt 606a so as to rotatably support the fourth belt 606a.

The second laterally driving part 606 is configured to apply a force in left and right directions to the fourth connecting bracket 602. For example, as shown in FIGS. 5A, 5B and 10, it may comprise a fourth belt 606a, a fourth motor 606b and a fourth driven pulley 606c. Herein, "applying a force in left and right or lateral directions to the fourth connecting bracket 602" may mean applying a force in left and right directions to the sample collection member 100 and the vertical moving unit 420 connected to the fourth connecting bracket 602 to thereby move them.

The fourth belt 606a extends long laterally and is fixed to the fourth connecting bracket 602 so as to transfer the power of the fourth 606b to the fourth connecting bracket 602. The fourth motor 606b is provided on one side of the fourth belt 606a so as to rotate the fourth belt 606a. The fourth driven pulley 606c is provided on the other side of the fourth belt 606a so as to rotatably support the fourth belt 606a. In particular, the pulley-belt type of the second laterally driving part 606 is provided which can prevent vibration and foreign matter from being caused by friction during lateral movement, unlike a gear type, so that more accurate testing can be achieved. Furthermore, the lateral vibration during a lateral movement can be prevented, and thus the optical reader 500 can be accurately moved laterally. In addition, the second laterally guiding rail 604a is configured to correspond to the second laterally guiding part 604b, and thus vibration may further be prevented.

As the second driving unit 600 is provided to move the optical reader 500, testing may be performed after the optical reader 500 is positioned over any one of the plurality of cuvettes 200 arranged in parallel.

Figure 20:
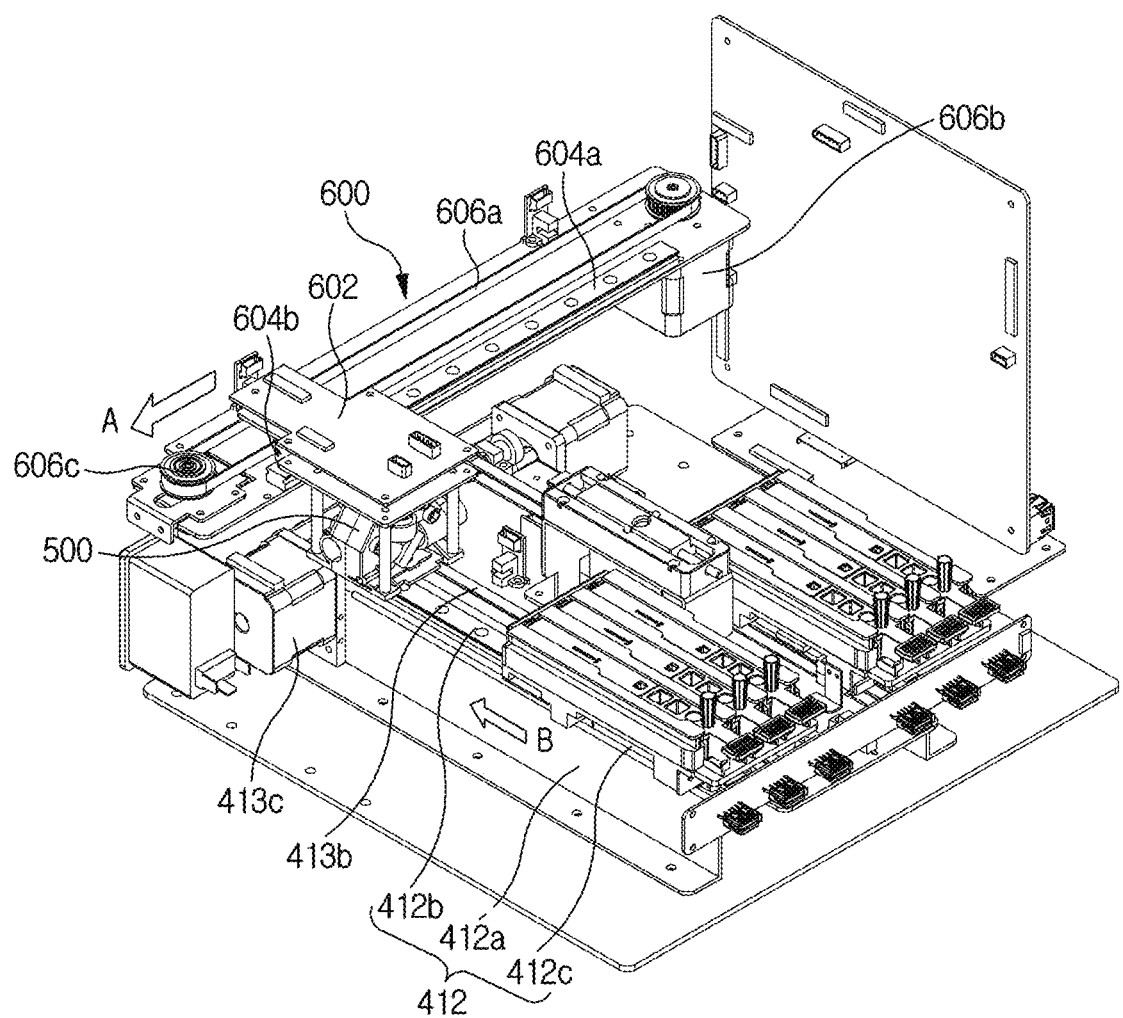
FIG. 20 schematically shows the operation of the second driving unit in the station shown in FIG. 1.

In addition, the station according to one embodiment of the present disclosure may further comprise: a printed circuit board (PCB) 900, 910 or 920 provided in the housing 300 as shown in, for example, FIG. 2B; and a control unit mounted on the printed circuit board and configured to control the first driving unit 400 and the optical reader 500. For example, as described above, the control unit controls the first driving unit 400 in the process in which the sample collection member 100 in the standby chamber 210 is bound to the arm 423 (see FIG. 15), the process in which the sample chamber 220, reagent chamber 230 and detection part 240 of the cuvette 200 are positioned under the sample collection member 100 and the sample collection member 100 is inserted into each chamber (see FIG. 16), and the process in which the sample collection member 100 is separated from the arm 423 (see FIG. 18), etc. In addition, it should be understood that the control unit may also control the second driving unit 600 as shown in FIG. 20.

Hereinafter, the process in which the cuvette 200 is mounted into the holder 411 will be described with reference to FIG. 13.

Figure 13:
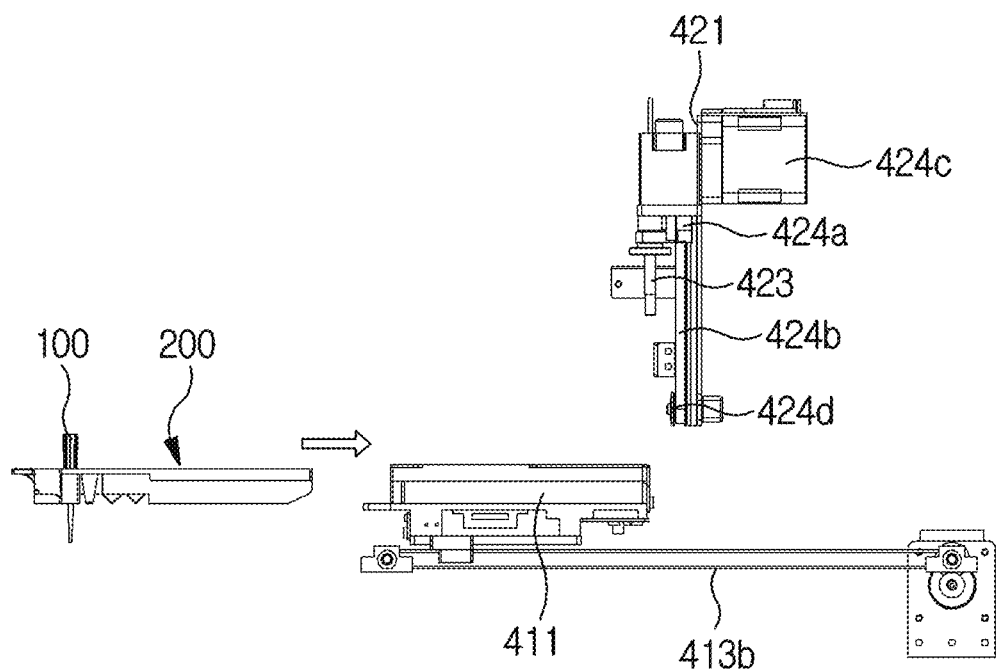
FIGS. 13, 14 and 15 are side views showing a process in which a cuvette enters the holder of a longitudinal moving unit.

FIG. 13 is a side view schematically showing the process in which the cuvette 200 is mounted into the holder 411 of the longitudinal moving unit.

As shown in FIG. 13, when the cuvette 200 is moved toward the holder 411 through the input/output part of the housing 300 in the direction of the arrow, the cuvette 200 is mounted into the holder 411 as shown in FIGS. 1 and 2. At this time, the sample collection member 100 is in the standby chamber 210 of the cuvette 200, the sample chamber 230 has a sample filled therein, and the detection part 240 is in an empty state.

Hereinafter, the process in which the sample collection member 100 in the standby chamber 210 is bound to the arm 423 will be described with reference to FIGS. 14 and 15.

Figure 14:
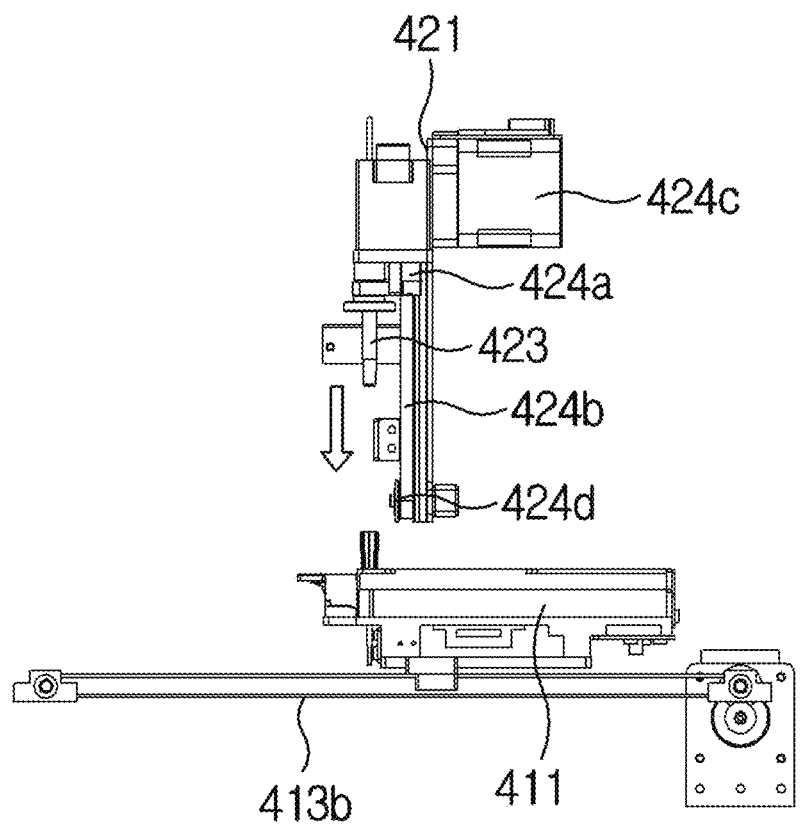
Figure 15:
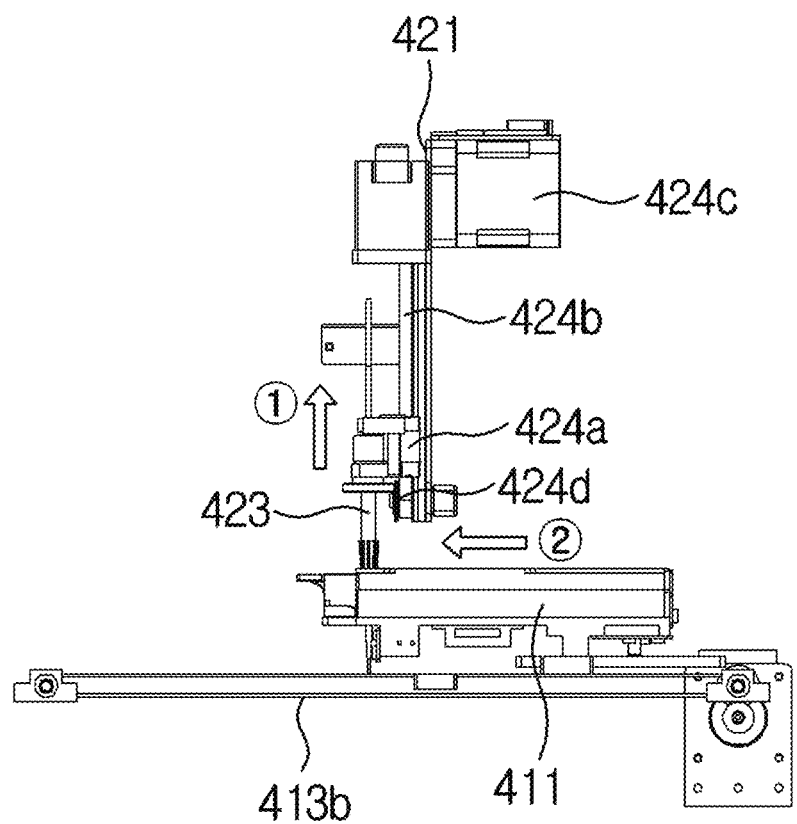

FIGS. 14 and 15 show the process in which the sample collection member 100 mounted in the cuvette 200 is bound to the arm 423 of the vertical moving unit in a state in which the holder 411 in FIG. 13 is removed.

When the cuvette 200 having the sample collection member 100 placed therein completely enters the holder 411, the holder 411 having the cuvette 200 received therein is then moved by the longitudinal moving unit 410. Then, as shown in FIG. 14, when the arm 423 is positioned over the sample collection member 100, movement of the holder 411 having the cuvette 200 by the longitudinal moving unit 410 is then stopped, and the sample collection member 100 is moved downward (arrow direction) by the vertical moving unit 420. Next, as shown in FIG. 15, the arm 423 is inserted into and bound to the sample collection member 100 by the downward force of the arm 423, the arm 423 is moved upward (arrow No. 1) by the vertical moving unit 420, and the holder 411 having the cuvette 200 received therein is moved in the left direction (see arrow number 2) in the figure by the longitudinal moving unit 410.

Hereinafter, the process in which the sample chamber 220, reagent chamber 230 and detection part 240 of the cuvette 200 are positioned under the sample collection member 100 and the sample collection member 100 is inserted into each chamber will be described with reference to FIG. 16.

FIG. 16 shows the process in which the sample chamber 220, reagent chamber 230 and detection part 240 of the cuvette 200 are positioned under the sample collection member 100 bound to the arm 423 while the cuvette 200 of FIG. 15 is moved forward and backward by the longitudinal moving unit 410.

As shown in FIG. 16(A), when the sample chamber 220 of the cuvette 200 is positioned under the sample collection member 100 while the cuvette 200 is moved in the left direction in the figure by the laterally moving unit 410, the sample collection member 100 is then moved in the downward direction in the figure by the vertical moving unit 420 and inserted into the sample chamber 220. At this time, the pump unit 440 is operated and a suitable amount of a sample in the sample chamber 220 is sucked in the sample collection member 100.

Thereafter, as shown in FIG. 16(B), when the reagent chamber 230 of the cuvette 200 is positioned under the sample collection member 100 while the cuvette 200 is moved in the left direction in the figure by the laterally moving unit 410, the sample collection member 100 is moved in the downward direction in the figure by the vertical moving unit 420 and inserted into the reagent chamber 230. At this time, the pump unit 440 is operated, and thus the reagent in the sample collection member 100 is mixed and reacted with the reagent of the reagent chamber 230, and a suitable amount of the reaction product is sucked in the sample collection member 100.

Next, as shown in FIG. 16(C), when the detection part 240 of the cuvette 200 is positioned under the sample collection member 100 while the cuvette 200 is moved in the right direction in the figure by the laterally moving unit 410, the sample collection member 100 is then moved in the downward direction in the figure by the vertical moving unit 420 and inserted into the detection part 240. At this time, the pump unit 440 is operated and the reaction product in the sample collection member 100 is discharged into the detection part 240.

Meanwhile, in embodiments, after the reaction product is discharged into the detection part 240, the cuvette 200 is moved in the right direction in the figure by the laterally moving unit 410, the detection part 240 enters the optical reader 500, and the reaction product in the detection part is analyzed by the optical reader 500.

Hereinafter, the process in which the sample collection member 100 is separated from the arm 423 will be described with reference to FIGS. 17 and 18.

Figure 17:
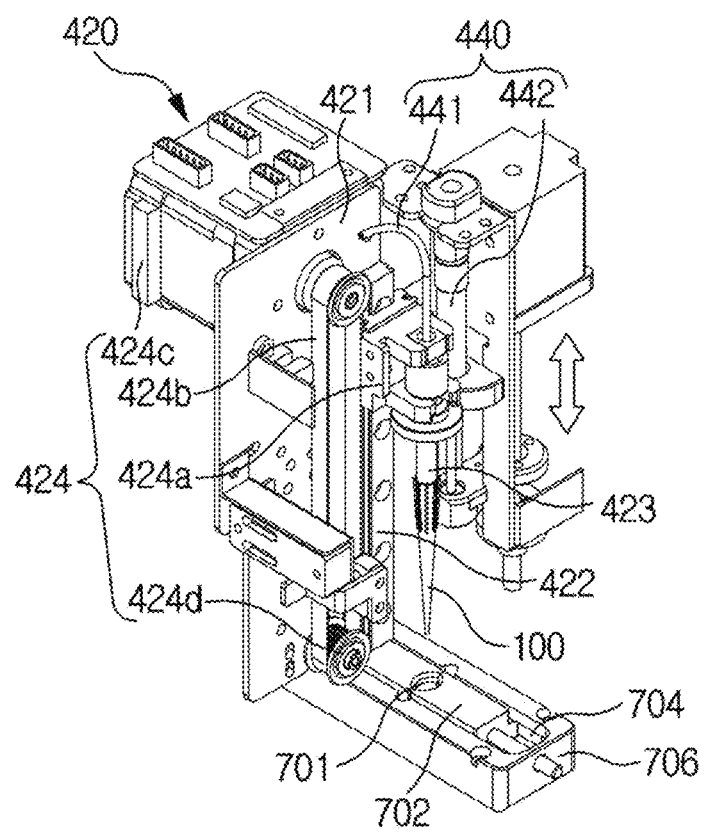
FIGS. 17 and 18 show a process in which a sample collection member is separated from an arm.
Figure 18:
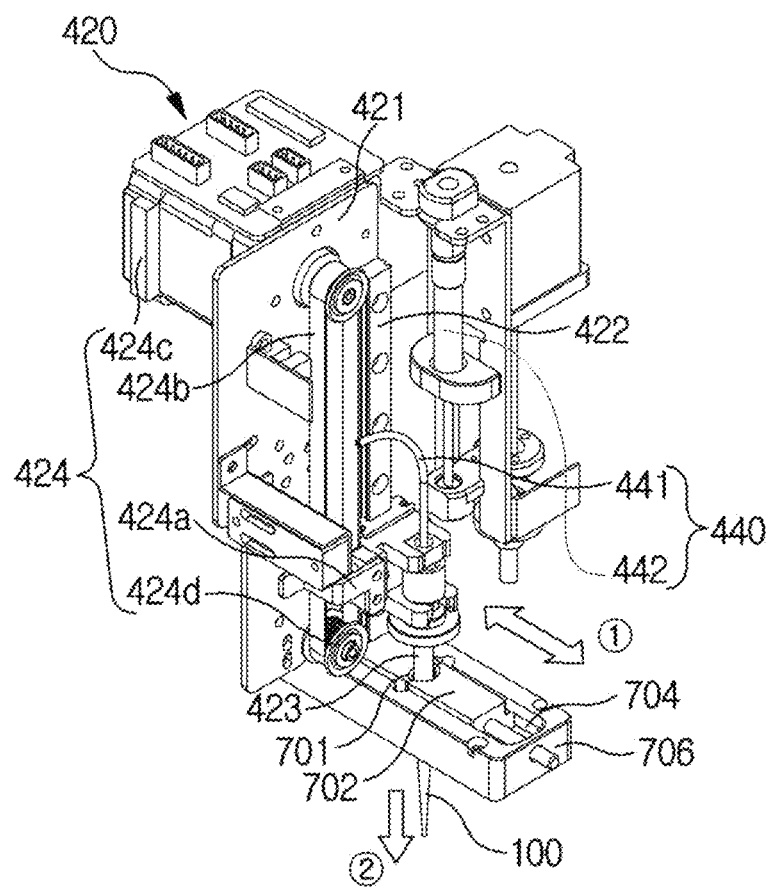

FIGS. 17 and 18 show the process in which the sample collection member 100 is separated from the arm 423.

As shown in FIG. 17, the sample collection member 100 is positioned over the removal unit 700 by the first laterally moving unit 430. At this time, as described above, the removal unit 700 is positioned on the path of left-and-right movement of the sample collection member 100. Then, the sample collection member 100 is moved in the downward direction in the figure by the vertical moving unit 420. Next, as shown in FIG. 18, the sample collection member 100 is inserted into the through-hole 701, and then the slider 702 slidably moves as indicated by arrow 1 to pull the sample collection member 100 inserted into the through-hole 701 in one direction. Then, as shown by arrow 2 in FIG. 18, the sample collection member 100 is separated from the arm 423, drops downward, and is collected in the waste box 708. At this time, as described above, the sample collection member 100 is made of a flexible material so that insertion of the sample collection member into the through-hole 701 and the resulting separation of the sample collection member 100 can be easily achieved. Meanwhile, as described above, a spring is provided in the removal unit 700 so that the slider 702 can be restored to the original position after its operation.

Hereinafter, the station according to one embodiment of the present disclosure will be explained in further detail.

As shown in FIG. 1, the station according to one embodiment of the present disclosure may further comprise a display unit 830 provided in the housing 300 and configured to display the analysis results obtained by the optical reader 500. Accordingly, the analysis results can be visually immediately displayed through the display unit 830, and thus rapid testing can be achieved.

In addition, the station according to the present disclosure may be used for simultaneous detection of a plurality of different analytes contained in a biological sample. In this aspect, as shown in FIG. 1, the station according to one embodiment of the present disclosure may further comprise: one or more chips provided in the housing 300, the chips having a recognition system comprising information about the a sample filled in the sample chamber 220, the kind of analytes to be detected in the sample, and/or a specific method for driving the station according to the sample; and a chip insertion part 820 into which the chip is inserted. The barcode is read by the barcode measurement part shown in FIG. 2B or a scanner 450, and this information is used in combination with the information stored in the chip inserted in the chip insertion part. The chip and the chip insertion part are controlled by a control unit mounted on the printed circuit board 930 at a position as shown in, for example, FIG. 2B. Thus, it is possible to input information through the chip and the chip insertion part 820 in a more rapid and accurate manner compared to inputting sample information and the like through a keyboard. Accordingly, the station can be driven so that optimal analysis can be performed depending on the kinds of plurality of various analytes, and thus various analytes can be easily detected by a single station, and the reproducibility and reliability of analysis can also be improved.

Figure 1B:
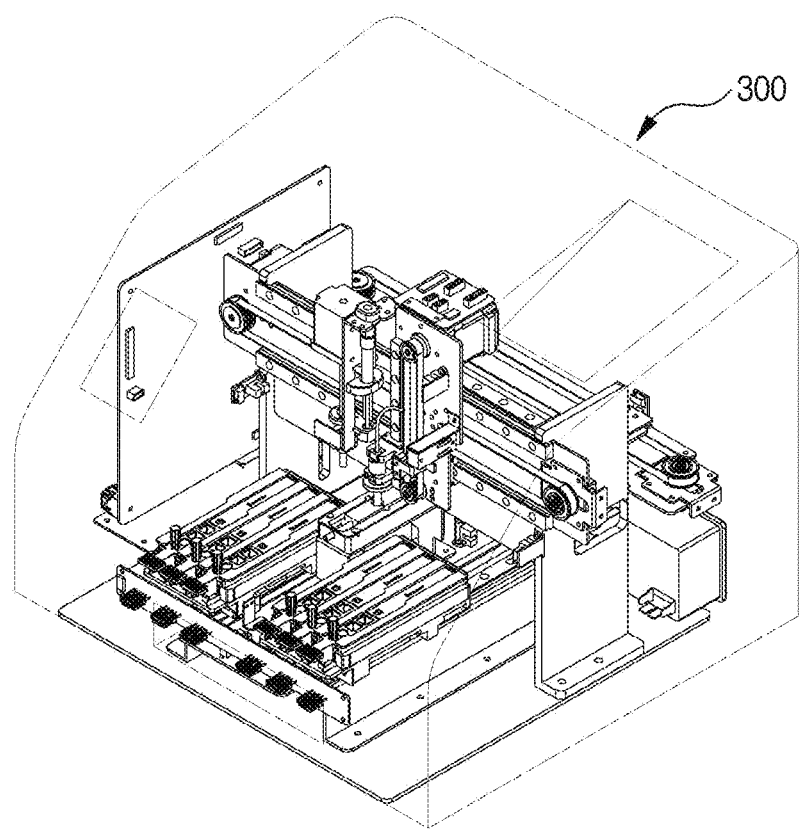
FIG. 1B is a perspective view schematically showing a station according to another embodiment of the present disclosure.

In addition, as shown in FIGS. 1A and 1B, the station according to one embodiment of the present disclosure is provided in the housing 300. It may further comprise a print/output part configured to print and output the results of analysis. Thus, the analysis results can be immediately provided as a document through the print/output part without having to use a separate printer.

In addition, the station according to one embodiment of the present disclosure may further comprise, in the housing 300, a door through which the plurality of cuvettes may enter and exit the station. Accordingly, the door may be closed during analysis in order to prevent foreign matter from entering the housing 300, and thus more accurate analysis can be performed.

In addition, the holder 411 may further comprise a heater configured to heat the holder 411, and a temperature sensor configured to sense the temperature of the holder 411. Thus, the sample received in the sample chamber 220, the reagent received in the reagent chamber 230, and the reaction product received in the detection part 240 may be maintained at suitable temperatures required in analysis.

In addition, the holder 411 may have specific sensors that senses whether or not the sample collection member 100 and the cuvette 200 would be mounted. The sensor that senses mounting of the sample collection member will now be described with reference to FIG. 7D. On the lower side of the sample collection member standby chamber 210 of the cuvette, into which the sample collection member 100 of the cuvette 200 is inserted, an opening through which the sample collection member can pass is formed, and on the holder, an opening is also formed at a portion corresponding to the opening of the standby chamber. Accordingly, when the sample collection member 100 passes through the cuvette and the holder, the sample collection member is sensed by an interrupt sensor 414 provided at the lower portion. The right of FIG. 7D is a top view of the holder, which shows various shapes of the opening formed in the holder. The upper portion of the right of FIG. 7D shows a structure enabling the sample collection member to be inserted into the holder after insertion of the cuvette, and the lower portion shows a structure enabling the cuvette to be inserted into the holder after insertion of the sample collection member. The sample collection member-sensing sensor as described above allows the user to check the start of the reading test of the presence or absence of the sample collection member before the start of analysis and to confirm the start of analysis and to determine whether the arm would be inserted into the sample collection member and would move upward. As shown in FIG. 7E, a sensor 411e, 411f that senses mounting of the cuvette is provided on the backside of the holder to make it possible to confirm that the holder 411 having cuvettes required for analysis was mounted in the system before the start of the analysis, thereby improving convenience, accuracy and reliability.

In addition, as shown in, for example, FIG. 2A, for arrangement and management of cables connected to moving members, the station according to one embodiment of the present disclosure may further comprise a longitudinal moving unit cable chain 850, a driving unit cable chain 860, and an optical reader cable chain 870. The position of the chain may be variable.

Hereinafter, steps of analyzing an analyte in a sample by use of the station according to one embodiment of the present disclosure will be described briefly.

After the cuvette is mounted into the holder of the station, the sample collection member is placed in the sample collection member standby chamber of the cuvette to allow insertion of the sample collection member to be recognized, and a start button for the station is clicked. Then, the cuvette moves backward, and then the information of the barcode is read by the barcode scanner, and this information is linked with the information of an ID chip, and thus the station is suitably driven depending on the kind of analyte. Accordingly, the arm is driven and a sample is suitably dispensed, and then a reaction between the sample and the reagent is performed at a specific temperature for a specific time. Next, the reaction product is dispensed into the detection part including lateral flow-type chromatography, and is developed in the chromatography membrane, and the resulting fluorescent signal is detected. Using this information, qualitative or quantitative results for a specific analyte contained in the sample are obtained. Each step appears through the display provided in the station. After completion of the analysis, the sample collection member is not present in the sample collection member standby chamber, and the cuvette is in a state mounted in the holder. This state is recognized, and a massage to remove the cuvette pops up, and the analysis is terminated.

FIGS. 22 to 25 show the system configuration of the station according to the present disclosure.

Figure 22:
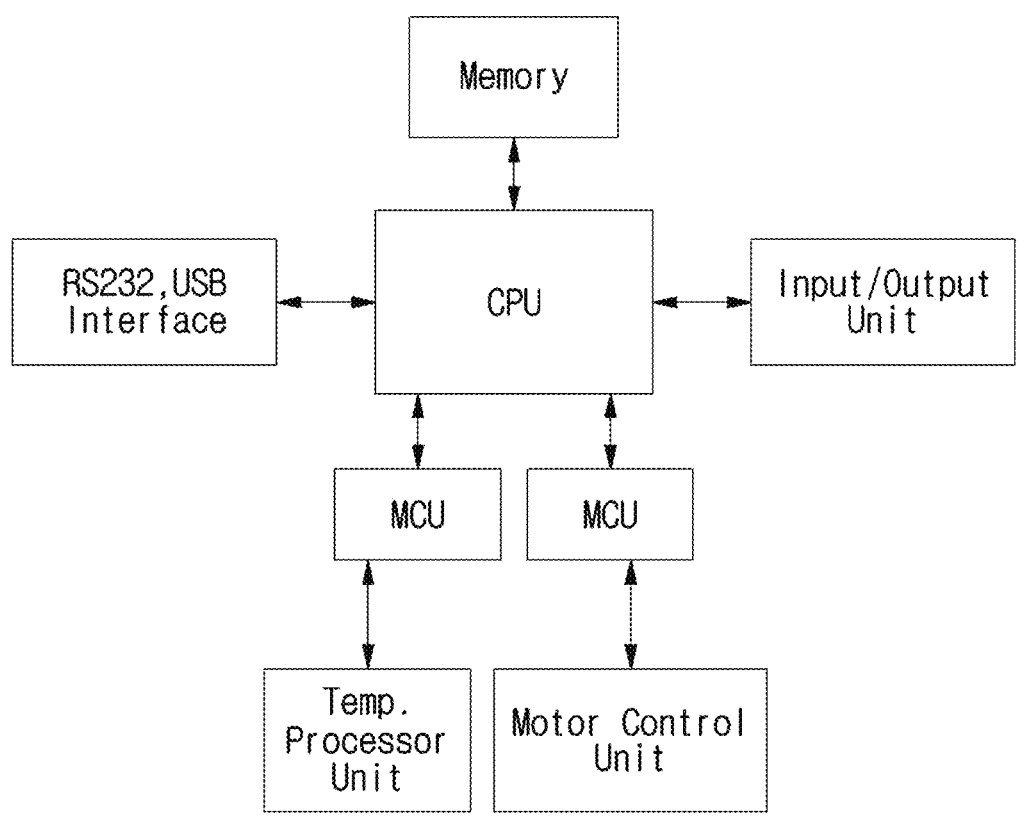
FIG. 22 shows the control configuration of the main system of the station according to the present disclosure.

FIG. 22 shows the control configuration of the main system. The main system is configured such that it can be operated with a central processor (CPU), a microprocessor, interfaces such as USB, RS232 and the like, a motor control unit, a system memory, a heating system, and an input/output system. The central processor unit (CPU) operates an operating system, and may send and receive commands to and from the system memory, the input/output system, RS232, USB interfaces, and the like. The microprocessor may be included in a controller, and may drive and control a motor control unit, a temperature control unit, and the like. The input/output system may comprise input devices such as a keyboard, a mouse, a touch pad and the like, and output devices such as a monitor, a printer and the like.

Figure 23:
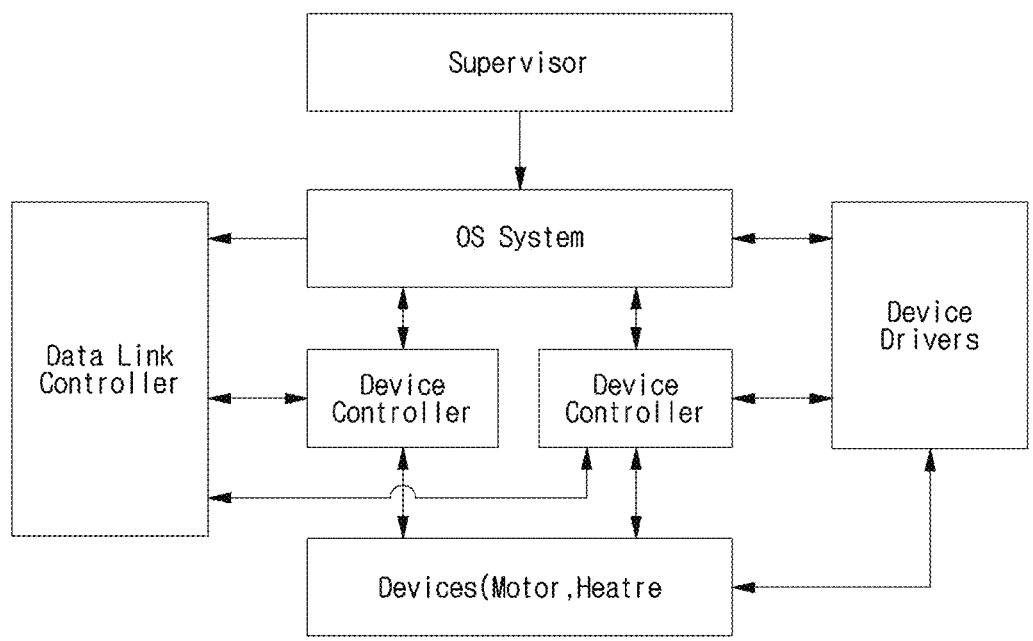
FIG. 23 is a block diagram showing the configuration of the operating system of the station according to the present disclosure.

FIG. 23 is a block diagram showing the configuration of an operating system. The operating system may comprise applications required for driving of various systems and input/output of information, and comprise separate controllers for data input/output (image output, printing, data storage, etc.).

The operating system may drive and control devices through device drivers, and may also be driven and controlled using device controllers including a microprocessor.

In the present disclosure, separate controllers may be provided for independent driving and control of each cartridge driving unit, and control operations such as heater control, reset and the like may also be performed directly by the operating system.

Figure 24:
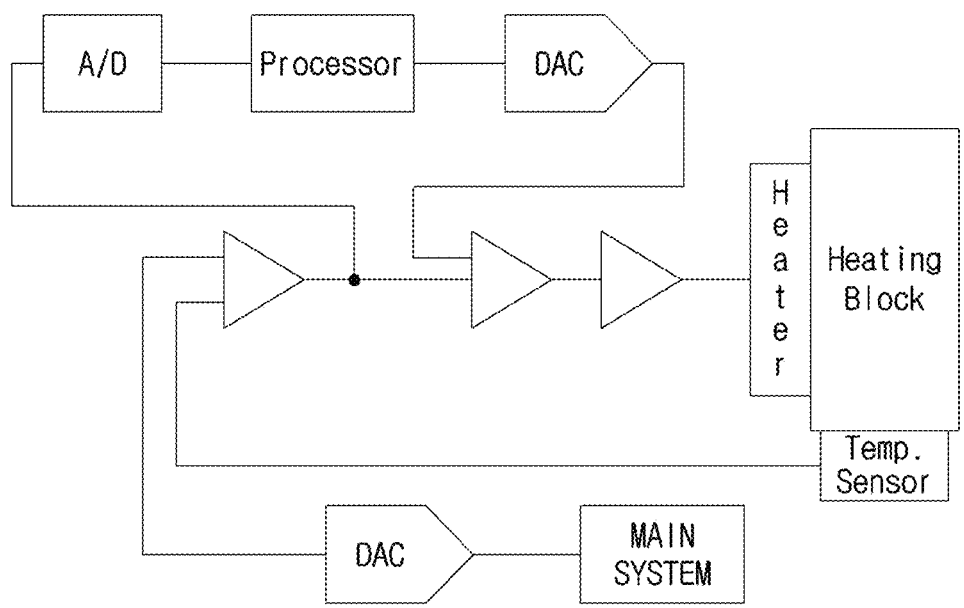
FIG. 24 is a block diagram showing the configuration of the cartridge heating system circuit of the station according to the present disclosure.

FIG. 24 is a block diagram showing the configuration of a cartridge heating system circuit. A digital signal from the CPU of the main system is controlled, converted to an analog signal, and amplified through an amplifier, and the amplified signal operates a heater through a driver. A temperature sensor is attached to a heater block, and a signal from the temperature sensor passes through the amplifier and processed in a processor. At this time, a predetermined temperature can be controlled to a constant temperature by a feedback circuit.

Figure 25:
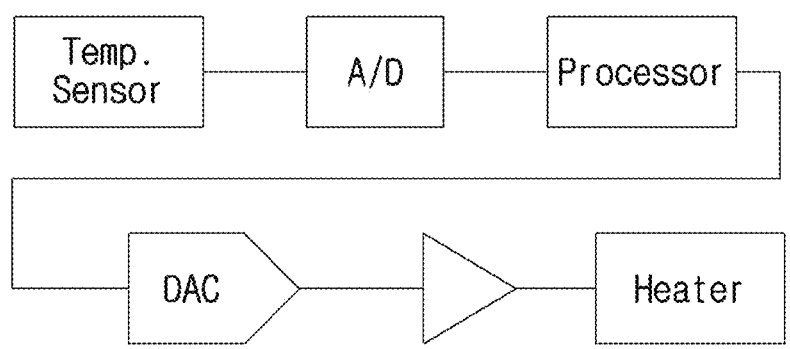
FIG. 25 is a block diagram showing the configuration of the heater control circuit of the station according to the present disclosure.
Figure 26:
FIG. 26 is a picture of a station according to an embodiment of the present disclosure.

FIG. 25 is a block diagram showing the configuration of a heater control circuit. The heater control circuit comprises a temperature sensor, an analog/digital signal converter, a processor, a digital/analog converter, a buffer and a heater. The heater control circuit is configured such that an analog signal from the temperature sensor is converted to a digital signal through the converter and that the heater is operated or stopped by a driver and can be controlled to a predetermined temperature.

Hereinafter, additional embodiments are further discussed.

System

Referring to FIGS. 1A-7B, 20, 21A and 21B, in embodiments, the system includes an analyzer (or a station) 300 and multiple cuvettes 200.

Cuvette

Each cuvette 200 has an elongated body including multiple wells 220 and 230 arranged along a longitudinal direction. The multiple wells include a sample well 220 into which a biological fluid sample is loaded for analysis. The multiple wells include one or more additional wells 230, each of which contains a liquid reaction composition. Each cuvette 200 further includes a chromatographic strip 20 arranged behind the multiple wells in the longitudinal direction.

Example of Cuvette

For example, referring to FIGS. 21A and 21B, the cuvette 200 includes the sample well 220, a first reaction well 230a and a second reaction well 230*b*, and a chromatographic strip 20 arranged along the longitudinal direction. The cuvette 200 further includes a liquid inlet or chromatographic inlet 32 connected to the chromatographic strip 20 for receiving liquid and letting the liquid flow into the chromatographic strip 20. In embodiments, the first reaction well 230*a* contains a first reaction composition in liquid, and the second reaction well 230*b* contains a second reaction composition in liquid. The liquid inlet 32 includes a passage way of the liquid and provides a temporary reservoir. Unlike the first and second reaction wells 230, the liquid inlet 32 does not contain a liquid material therein.

Analyzer

The analyzer 300 includes a pipette, a pipette mechanism 400, at least one optical device 500, an optical device mechanism 600, at least one cuvette holder 411 and at least one cuvette holder mechanism 413. For the sake of convenience of description, the analyzer 300 has x, y and z axes that are perpendicular to each other. (See FIG. 2A.) The x and y axes define a horizontal plane. The pipette may be referred as a sample collection member.

Pipette Mechanism

The pipette mechanism 400 includes displacement mechanism and suction mechanism. The displacement mechanism is configured to move the pipette along the x axis and further along the z axis. The displacement mechanism is not configured to move the pipette in the y axis. The suction mechanism or pump unit 440 is configured to operate the pipette to take and release liquid.

Optical Device and Optical Device Mechanism

The at least one optical device 500 includes at least one light source and at least one light detector. In embodiments, the optical device 500 may include one laser beam source and a laser beam detector and further includes one LED light source and one LED light detector. The optical device mechanism 600 is configured to move the at least one optical device 500 together or individually along the x axis. In embodiments, however, the optical device mechanism 600 does not move the optical device 500 along the y or z axes.

Cuvette Holder

Each cuvette holder or cuvette bay 411 includes multiple cuvette slots. Each cuvette slot is configured to receive a cuvette 200.

Cuvette Holder Mechanism

The cuvette holder mechanism 413 is configured to move the at least one cuvette holder together and/or individually along the y axis. In embodiments, however, the cuvette holder mechanism 413 does not move the cuvette holder along the x or z axis.

Loading a Sample Fluid

An operator loads a test sample into the sample well of the cuvette 200 before or after loading the cuvette 200 into the cuvette holder 411. The test sample includes a biological sample fluid obtained from human or animal.

Loading the Cuvette

The operator inserts the sample-loaded cuvette 200*a* cuvette slot of the cuvette holder 411. Multiple cuvettes may be loaded in one cuvette holder. In one embodiments, the chromatographic strip includes one end portion onto which a reaction mixture or reaction product from the multi-wells is loaded through a liquid inlet 32.

Suction Tip

Each cuvette 200 may include a suction tip holder 210 or an opening for receiving a suction tip 100 for the pipette. The operator may place one suction tip 100 into the suction tip holder 210 before or after loading the cuvette 200 into the cuvette holder 411. In some embodiments, the cuvette 200 does not include a suction tip holder or opening for receiving a new suction tip.

Initiating Analyzer

Subsequently, the operator initiates a sample analysis, for example, by pressing an initiation button of the analyzer. Then, the automated process of sample analysis is performed by the analyzer 300. In the following discussions, the parallel and sequential actions by the components of the analyzer 300 are performed in accordance with software and/or command parameters inputted into the analyzer.

Moving Cuvette Holder

During operation, the cuvette holder mechanism 413 moves each cuvette holder 411 along the y axis such that the pipette is located over various locations of the cuvette 200.

Mounting Suction Tip

Initially, the cuvette holder mechanism 413 moves at least one cuvette holder 411 in a direction of the y axis toward where the pipette is located inside the analyzer. The cuvette holder 411 travels to a point in the y axis such that the pipette is located above the suction tip 100 of a first cuvette 200*a* among the multiple cuvettes held by the cuvette holder 411. Then, the pipette mechanism 400 moves the pipette down along the z axis such that a distal end portion of the pipette is inserted into the top opening of the suction tip 100, by which the suction tip 100 is mounted at the distal end of the pipette.

Taking Test Sample

Subsequently, the cuvette holder 411 travels to a point in the y axis such that the pipette is located above the sample well 220 of the first cuvette 200*a*. Then, the pipette displacement mechanism 400 moves the pipette down along the z axis such that the suction tip is inserted into the sample well 220. The pipette suction mechanism then takes a portion of the test sample contained in the sample well 220. Then, the pipette displacement mechanism 400 moves the pipette up along the z axis.

Mixing into the First Reaction Well

Subsequently, the cuvette holder 411 travels to a point along the y axis such that the pipette is located above the first reaction well 230*a* of the first cuvette 200*a* that contains a first reaction composition. Then, the pipette displacement mechanism 400 moves the pipette down along the z axis such that the suction tip 100 is inserted into the first reaction well 230*a*. The pipette suction mechanism 440 then releases into the first reaction well 230*a* the test sample taken from the sample well 220. Then, optionally, the pipette displacement mechanism 400 moves the pipette up along the z axis.

Taking First Reaction Mixture

The pipette mechanism lets a predetermined time pass for one or more reactions between the test sample and the first reaction composition in the first reaction well 230*a*. After the predetermined time has passed, the pipette displacement mechanism 400 and the suction mechanism 440 operate such that the pipette takes a reaction mixture (first reaction mixture) from the first reaction well 230*a*.

Mixing into the Section Reaction Well

Optionally, when the cuvette 200 includes a second reaction well 230*b*, the cuvette holder 411 travels to a point along the y axis such that the pipette is located above the second reaction well 230*b* of the first cuvette 200*a* that contains a second reaction composition. Then, the pipette displacement mechanism 400 moves the pipette down along the z axis such that the suction tip 100 is inserted into the second reaction well 230*b*. The pipette suction mechanism 440 then releases into the second reaction well 230*b* the first reaction mixture taken from the first reaction well 230*a*. Then, optionally, the pipette displacement mechanism 400 moves the pipette up along the z axis.

Taking Second Reaction Mixture

After a predetermined time has passed for one or more reactions between the first reaction mixture and the second reaction composition in the second reaction well 230a, the pipette displacement and suction mechanisms 400 and 440 operate such that the pipette takes a reaction mixture (second reaction mixture) from the second reaction well 230b.

Chromatography

Subsequently, the cuvette displacement mechanism 413 operates such that the cuvette holder 411 travels to a point in the y axis in which the pipette is located over the liquid inlet 32 of the first cuvette. Then, the pipette displacement and suction mechanisms 400 and 440 operate such that the pipette moves down along the z axis and releases reaction mixture (either first reaction mixture or second reaction mixture) into the liquid inlet 32 which contains no liquid material. The reaction mixture, after passing the reservoir of the liquid inlet, follows into the chromatographic strip along the y axis. In embodiments, the chromatographic strip includes a chemical entity specific to a biomarker at a predetermined location along the y axis. When the reaction mixture includes the particular biomarker, the biomarker is trapped at the predetermined location and other chemical entities contained in the reaction mixture flow through the chromatographic strip. In another embodiment, the reaction mixture includes the particular biomarker and a particular chemical entity connected to the biomarker, the particular biomarker and the particular chemical entity are trapped at the predetermined location of the chromatographic strip and other chemical entities contained in the reaction mixture flow through the chromatographic strip. In embodiments, the trapped chemical entity may include a fluorescent substance.

Optical Detection

Once the chromatographic flow has completed, the cuvette displacement mechanism 413 causes the cuvette holder 411 to travel along the y axis such that the chromatographic strip 20 is located under the at least one optical device 500 for optical detection of the biomarker or any other chemical entity connected to the biomarker.

Removing Suction Tip

Once the pipette releases the reaction mixture into the liquid inlet 32, the pipette displacement mechanism 400 moves the pipette in the x axis toward a suction tip disposal location or suction tip disengagement location 700 before, during and/or after the optical detection. At the suction tip disposal location 700, the pipette displacement mechanism 400 moves the pipette down and up in the z axis to remove and dispose the suction tip 100 that has been used in connection with the first cuvette 200a.

Operation for the Next Cuvette

Subsequently, the analyzer 300 initiates similar operations for the next cuvette, here the second cuvette 200b in the same cuvette holder. All of the foregoing process steps from mounting a suction tip through optical detection will be performed for the second cuvette 200b except any optional steps.

Supplying New Suction Tips

In embodiments where the cuvette does not include a suction tip holder, the analyzer 300 may include a suction tip engaging location, in which the pipette engages with a new suction tip after removing the used suction tip before the processing for the next cuvette.

Chromatographic Flow Time Varies

The time for chromatographic flow may vary depending upon tests. This is because certain chemical entities flow faster than others, and the reaction mixture for chromatographic flow may not be the same all the time.

Long Chromatographic Flow

When the chromatographic flow is expected to be longer than a predetermined reference time, the transition to the second cuvette 200b occur before the competition of the chromatographic flow in the first cuvette 200a. For example, when a particular test or analysis of the sample requires a chromatographic flow longer than a predetermined reference time, the pipette displacement mechanism 400 moves the pipette in the x axis toward the second cuvette 200b, and the cuvette mechanism 413 moves the cuvette holder 411 in the y axis such that the pipette is placed over the suction tip 100 of the second cuvette 200b. Subsequently, the pipette displacement mechanism 400 moves the pipette for engaging with the suction tip 100 of the second cuvette 200b and the subsequent steps continues for the second cuvette 200b up to releasing the reaction mixture into the liquid inlet 32 of the second cuvette 200b. During the pipette operations for the second cuvette 200b, no optical detection for the first cuvette 200a is performed. The optical detection for the first cuvette 200a is performed only after the completion of the pipette operations for the second cuvette 200b, i.e., from taking the test sample of the second cuvette 200b to releasing reaction mixture into the liquid inlet 32 of the second cuvette 200b.

Short Chromatographic Flow

When the chromatographic flow is expected to be shorter than the predetermined reference time, the transition to the second cuvette occurs after the competition of the chromatographic flow in the first cuvette. For example, when a particular test or analysis of the sample requires a chromatographic flow shorter than a predetermined reference time, the pipette operations for the second cuvette 200b is deferred to until after optical detection for the first cuvette 200a. Thus, the pipette operations for the second cuvette 200b, i.e., from taking the test sample of the second cuvette 200a to releasing reaction mixture into the liquid inlet 32 of the second cuvette 200b will be performed only after optical detection for the first cuvette 200a.

Time Charts

Figure 27A:
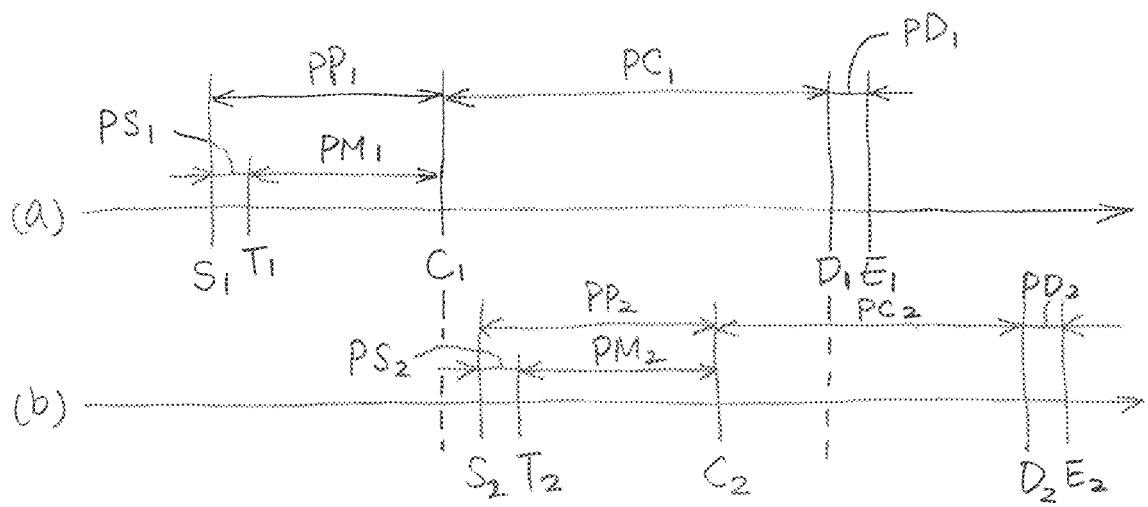
FIGS. 27A and 27B shows time charts of operating a biological fluid analysis system.
Figure 27B:
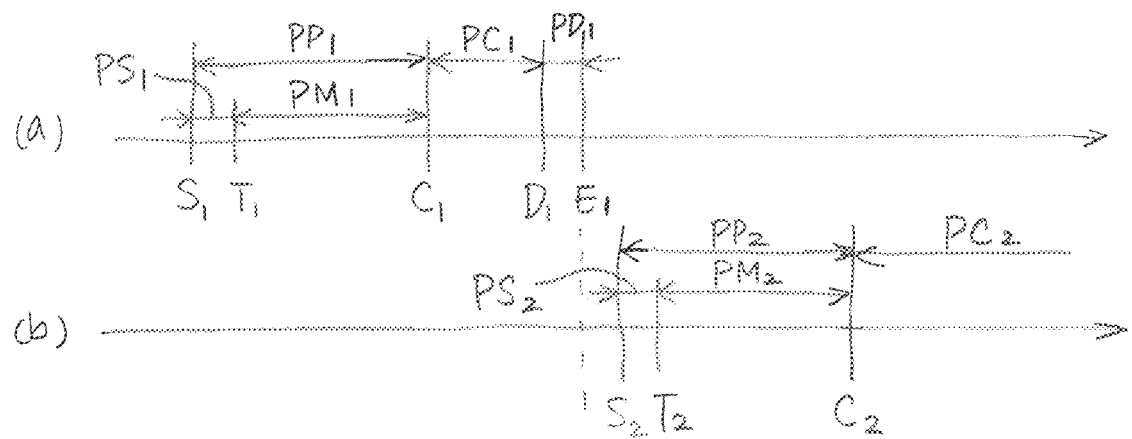

FIG. 27A shows an example time chart of the operation of the analyzer as discussed above under the heading "Long Chromatographic Flow," and FIG. 27B shows another example time chart of the operation of the analyzer as discussed above under the heading "Short Chromatographic Flow." Specifically, (a) of FIG. 27A and (a) of FIG. 27B show time charts of processing the sample fluid in the first cuvette, performing chromatography for the first cuvette and performing optical detection for the first cuvette. Further, (b) of each of FIG. 27A and (b) of FIG. 27B show time charts of processing the sample fluid in the second cuvette, performing chromatography for the second cuvette and performing optical detection for the second cuvette.

Time Periods and Time Points in the Time Charts

In FIGS. 27A and 27B, PP1 refers to a time period for processing the sample in the first cuvette. PP1 includes PM1 which refers to a time period from a time point T1 of taking the sample fluid in the sample well of the first cuvette to a time point C1 of releasing the reaction mixture in the first cuvette into the liquid inlet 32 for chromatography. C1 may be a time point of loading the reaction mixture on the chromatographic in the first cuvette or a time point of starting chromatography. PP1 may include PS1 which refers to a time period for engaging the first suction tip for the first cuvette. PS1 may be a time period from a time point S1 of starting movement of the cuvette holder along y axis for engagement of a suction tip to the time point T1. PC1 refers to a time period for chromatography for the first cuvette. In embodiments, PC1 may be predetermined depending on types of biological sample, types of chemical entity, and/or types of reaction compositions used in the first cuvette. PC1 can be a time period sufficient for the chemical entity in the reaction mixture to bind to a corresponding entity fixed on the strip at the predetermined position. PD1 refers to a time period for detecting the chemical entity. Similarly, in FIGS. 27A and 27B, PP2 refers to a time period for processing the sample in the second cuvette. PP2 includes PM2 which refers to a time period from a time point T2 of taking the sample fluid in the sample well of the second cuvette to a time point C2 of releasing the reaction mixture in the second cuvette into the liquid inlet 32 for chromatography. C2 may be a time point of loading the reaction mixture on the chromatographic in the second cuvette or a time point of starting chromatography. PP2 may include PS2 which refers to a time period for engaging the second suction tip for the second cuvette. PS2 may be a time period from a time point S2 of starting movement of the cuvette holder for engagement of a suction tip to the time point T2. PC2 refers to a time period for chromatography for the second cuvette. In embodiments, PC2 may be predetermined depending on types of biological sample, types of chemical entity, and/or types of reaction compositions used in the second cuvette. PC2 can be a time period sufficient for the chemical entity in the reaction mixture to bind to a corresponding entity fixed on the strip at the predetermined position. PD2 refers to a time period for detecting the chemical entity. In embodiments, when the analyzer carries suction tips at a certain fixed location in the analyzer 300 other than cuvettes placed in the cuvette holder, the processing time period PP1 or PP2 may exclude the suction tip engaging time period PS1 or PS2. The above time periods PP1, PC1, PD1, PM1, PS1, PP2, PC2, PD2, PM2 and PS2 can be predetermined according to a target biomarker, reaction compositions and chemical entity for chromatography of each cuvette. A storage of the analyzer 300 may store the information of the time periods discussed above.

Time Chart for Long Chromatographic Flow

As shown in FIG. 27A, in embodiments, the chromatography time period PC1 for the first cuvette is longer than the sample processing time PP2 for the second cuvette. Thus, the sample processing for the second cuvette is completed before the detection period PD1 for the first cuvette.

Time Chart for Short Chromatographic Flow

As shown in FIG. 27B, in embodiments, the chromatography time period PC1 for the first cuvette is shorter than the sample processing time PP2 or PM2 for the second cuvette. Thus, the sample processing for the second cuvette starts only after the detection period PD1 for the first cuvette.

Logical blocks, modules or units described in connection with embodiments disclosed herein can be implemented or performed by a computing device having at least one processor, at least one memory and at least one communication interface. The elements of a method, process, or algorithm described in connection with embodiments disclosed herein can be embodied directly in hardware, in a software module executed by at least one processor, or in a combination of the two. Computer-executable instructions for implementing a method, process, or algorithm described in connection with embodiments disclosed herein can be stored in a non-transitory computer readable storage medium.

Although embodiments of the present disclosure have been described in detail, those skilled in the art will appreciate that the scope of the present disclosure is not limited to the embodiments and various modifications and improvements are possible, without departing from the scope and spirit of the disclosure as disclosed in the accompanying claims.

What is claimed is:

1. A method of analyzing biological sample fluid, the method comprising:

placing a plurality of cuvettes side by side in an analyzer, each of the plurality of cuvettes comprising biological sample fluid,
wherein each cuvette comprises an elongated body with multiple wells and a chromatography inlet that are arranged along a longitudinal direction, wherein the multiple wells comprise a sample well into which the sample fluid is loaded for analysis, wherein the multiple wells further comprise at least one reaction well that contains a reaction composition, wherein each cuvette further comprises a chromatographic strip arranged behind the multiple wells in the longitudinal direction, the chromatographic strip comprising one end portion fluid communication with the chromatography inlet such that fluid received through the chromatography inlet is loaded at the end portion of the chromatographic strip, processing a first sample fluid contained in the sample well of a first cuvette of the plurality of cuvettes placed in the analyzer using at least one reaction composition contained in the at least one reaction well of the first cuvette to obtain a first reaction mixture, wherein the processing the first sample fluid is performed within a first sample processing time period;

subsequent to processing the first sample fluid, performing chromatography of the first reaction mixture in a first chromatographic strip of the first cuvette for a first chromatography time period;

subsequent to performing the chromatography of the first reaction mixture, performing optical detection of a first chemical entity connected to a first biomarker in the first chromatographic strip of the first cuvette;

subsequent to processing the first sample fluid, processing a second sample fluid contained in the sample well of a second cuvette of the plurality of cuvettes placed in the analyzer using at least one reaction composition contained in the at least one reaction well of the second cuvette to obtain a second reaction mixture, wherein the processing the second sample fluid is performed within a second sample processing time period;

subsequent to processing the second sample fluid, performing chromatography of the second reaction mixture in a second chromatographic strip of the second cuvette for a second chromatography time period; and subsequent to performing the chromatography of the second reaction mixture, performing optical detection of a second chemical entity connected to a second biomarker in the second chromatographic strip, wherein, when the first chromatography time period is longer than the second sample processing time period, processing the second sample fluid is performed before the optical detection for the first cuvette while processing the second sample fluid is performed after the optical detection for the first cuvette when the first chromatography time period is shorter than the second sample processing time period.

2. The method of claim 1, wherein the analyzer comprises a pipette comprising a pump, a tube connected to the pump and an arm connected to the tube, wherein processing the first sample fluid comprises:
  engaging a first suction tip with the arm,
  taking, using the pipette with the first suction tip, the first sample fluid from the sample well of the first cuvette,
  releasing, using the pipette with the first suction tip, the first sample fluid into the at least one reaction well of the first cuvette to obtain the first reaction mixture,
  taking, using the pipette with the first suction tip, at least a portion of the first reaction mixture from the at least one reaction well,
  releasing, using the pipette with the first suction tip, the first reaction mixture into the chromatography inlet of the first cuvette,
  disengaging the first suction tip from the arm;
wherein processing the second sample fluid comprises:
  engaging the second suction tip with the arm,
  taking, using the pipette with a second suction tip, the second sample fluid from the sample well of the second cuvette,
  releasing, using the pipette with the second suction tip, the second sample fluid into the at least one reaction well of the second cuvette,
  taking, using the pipette with the second suction tip, at least a portion of the second reaction mixture from the at least one reaction well of the second cuvette, and
  releasing, using the pipette with the second suction tip, the second reaction mixture into the chromatography inlet of the second cuvette,
  disengaging the second suction tip from the arm;
wherein the first sample processing time period is equal to or longer than a time period from taking the first sample fluid to releasing the first reaction mixture, wherein the second sample processing time period is equal to or longer than a time period from taking the second sample fluid to releasing the second reaction mixture.

3. The method of claim 2, wherein the analyzer comprises:
  a cuvette holder comprising a plurality of walls defining a plurality of channels that contain the plurality of cuvettes; and
  an optical detector comprising a light source and a light detector for performing the optical detection,
  wherein the method further comprises moving the cuvette holder along in y axis for placing the first cuvette under the optical detector such that the first chromatographic strip is located at a first optical detection location,
  wherein while the first chromatographic strip is located at the first optical detection location, the pipette is located at a location immediately above the second cuvette such that the pipette overlaps the second cuvette when viewed along z axis.

4. The method of claim 3, further comprising:
  before processing the first sample fluid, moving the pipette along z axis to engage the first suction tip;
  after processing the first sample fluid, moving the pipette along x axis from a pipette location over the first cuvette to a disengagement location of the analyzer;
  subsequently moving the pipette along z axis to remove the first suction tip from the pipette at the disengagement location; and
  wherein the pipette moves from the pipette location of the first cuvette to the disengagement location while performing chromatography for the first cuvette and while the cuvette holder is moving along y axis.

5. The method of claim 3, wherein the cuvette holder is referred to as a first cuvette holder, wherein the analyzer further comprises a second cuvette holder comprising a plurality of walls defining a plurality of cuvette channels,
  wherein process sample fluid is performed in one of the plurality of cuvettes in the second cuvette holder while optical detection is performed in one of the plurality of cuvettes in the first cuvette holder.

6. The method of claim 2, further comprising:
  before processing the first sample fluid, moving the pipette along z axis to engage the first suction tip;
  after processing the first sample fluid, moving the pipette along x axis from a first pipette location over the first cuvette to a disengagement location of the analyzer;
  subsequently moving the pipette along z axis to remove the first suction tip from the pipette at the disengagement location; and
  subsequently moving the pipette along x axis to a second pipette location over the second cuvette different from the first pipette location,
  wherein the pipette moves from the first pipette location of the first cuvette to the second pipette location over the second cuvette via the disengagement location while performing chromatography for the first cuvette.

7. The method of claim 1, wherein the optical detection for the first cuvette is not performed while processing the second sample fluid.

8. The method of claim 1, wherein the first sample fluid is obtained from a first person and the second sample fluid is obtained from a second person different from the first person, wherein the first biomarker is different from the second biomarker.

9. The method of claim 1, wherein the optical detection of the second chemical entity in the second chromatographic strip is performed prior to the optical detection of the first chemical entity in the first chromatographic strip.

10. The method of claim 1, wherein the optical detection of the second chemical entity in the second chromatographic strip is performed after the optical detection of the first chemical entity in the first chromatographic strip.

11. The method of claim 1, further comprising, subsequent to processing the second sample fluid, processing a third sample fluid contained in the sample well of a third one of the plurality of cuvettes placed in the analyzer using at least one reaction composition contained in the at least one reaction well of the third cuvette to obtain a third reaction mixture,
  wherein processing the third sample fluid is performed before the optical detection for the first cuvette.

12. The method of claim 11, wherein the optical detection for the first cuvette and optical detection for the second cuvette are not performed while processing the third sample fluid.

13. The method of claim 1, further comprising, subsequent to processing the second sample fluid, processing a third sample fluid contained in the sample well of a third one of the plurality of cuvettes placed in the analyzer using at least one reaction composition contained in the at least one reaction well of the third cuvette to obtain a third reaction mixture,
  wherein the optical detection for the first cuvette is performed between performing processing of the second sample fluid and performing processing of the third sample fluid.

14. The method of claim 13, wherein the optical detection for the second cuvette is not performed while processing the third sample fluid.

\* \* \* \* \*